United States Patent
Takahashi

(10) Patent No.: US 11,278,186 B2
(45) Date of Patent: Mar. 22, 2022

(54) ENDOSCOPE SYSTEM AND OPTICAL ADAPTOR FOR ENDOSCOPE

(71) Applicant: OLYMPUS CORPORATION, Tokyo (JP)

(72) Inventor: Susumu Takahashi, Iruma (JP)

(73) Assignee: OLYMPUS CORPORATION, Tokyo (JP)

(*) Notice: Subject to any disclaimer, the term of this patent is extended or adjusted under 35 U.S.C. 154(b) by 46 days.

(21) Appl. No.: 16/813,992

(22) Filed: Mar. 10, 2020

(65) Prior Publication Data
US 2020/0288946 A1 Sep. 17, 2020

(30) Foreign Application Priority Data
Mar. 13, 2019 (JP) .............................. JP2019-045765

(51) Int. Cl.
*A61B 1/00* (2006.01)
*A61B 1/06* (2006.01)
*A61B 1/005* (2006.01)
*A61B 1/05* (2006.01)

(52) U.S. Cl.
CPC ...... *A61B 1/00096* (2013.01); *A61B 1/00013* (2013.01); *A61B 1/00121* (2013.01); *A61B 1/0051* (2013.01); *A61B 1/051* (2013.01); *A61B 1/0676* (2013.01); *A61B 1/0684* (2013.01)

(58) Field of Classification Search
CPC ............ A61B 1/00096; A61B 1/00121; A61B 1/00013; A61B 1/0676; A61B 1/0051; A61B 1/0684; A61B 1/051; A61B 1/00101; A61B 1/05; G02B 23/2476; G02B 23/243; G02B 27/0025

USPC .......................................................... 600/175
See application file for complete search history.

(56) References Cited

U.S. PATENT DOCUMENTS

| | | | | |
|---|---|---|---|---|
| 5,916,148 A | * | 6/1999 | Tsuyuki | ............. A61B 1/00096 600/176 |
| 2010/0091385 A1 | * | 4/2010 | Togino | ................. G02B 17/004 359/736 |
| 2010/0259835 A1 | * | 10/2010 | Asami | .................... G02B 13/06 359/687 |
| 2017/0108678 A1 | * | 4/2017 | Miyazawa | ........... G02B 15/173 |

FOREIGN PATENT DOCUMENTS

| JP | H01-269909 A | | 10/1989 |
|---|---|---|---|
| JP | 2012047909 A | * | 3/2012 |
| JP | 2016-151629 A | | 8/2016 |

* cited by examiner

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope apparatus includes a removable optical adaptor and a main body optical system. The optical adaptor includes an aperture and includes a first group optical system having a negative combined focal length as a whole and a second group optical system having a positive combined focal length as a whole in order from an object side. The main body optical system includes an imaging lens configured to form an image of a light flux on an image pickup device, the light flux being transmitted through the adaptor from the object. The first group optical system includes a lens having an Abbe number of 35 or higher, and the second group optical system includes a lens having an Abbe number of 45 or lower.

15 Claims, 29 Drawing Sheets

FIG. 7

| # | | Radius | Thickness | Material | | Semi-Diameter | (n−1)/r surface_power |
|---|---|---|---|---|---|---|---|
| | | | | nd | νd | | |
| 0 | object | 44.301 | 13.069 | | | 38.338 | |
| 1 | L01 | 8.513 | 0.886 | 1.8830 | 40.8 | 4.430 | 0.22120 |
| 2 | | 2.306 | 1.329 | | | 2.038 | -0.81660 |
| 3 | L02 | Infinity | 0.631 | 1.6968 | 55.5 | 3.323 | 0 |
| 4 | | 2.027 | 0.997 | | | 1.108 | -0.83718 |
| 5 | L03 | -1.477 | 0.775 | 1.6516 | 58.6 | 0.842 | -1.11787 |
| 6 | | Infinity | 0.997 | 1.9229 | 18.9 | 1.108 | 0 |
| 7 | | -14.770 | 0.310 | | | 1.108 | 0.13019 |
| 8 | L04 | 9.095 | 0.997 | 1.9229 | 18.9 | 1.440 | 0.21142 |
| 9 | Stop(APERTURE) | Infinity | 0.111 | | | 0.428 | 0 |
| 10 | L05 | Infinity | 1.174 | 1.4875 | 70.2 | 1.440 | 0 |
| 11 | | -2.698 | 0.111 | | | 1.440 | 0.55134 |
| 12 | L06(CG) | Infinity | 0.886 | 1.5163 | 64.1 | 1.772 | 0 |
| 13 | | Infinity | 0.554 | | | 1.772 | 0 |
| 14 | L01(main-body) | Infinity | 0.886 | 1.5163 | 64.1 | 1.551 | |
| 15 | | Infinity | 0.222 | | | 1.551 | |
| 16 | L02(main-body) | 5.356 | 0.665 | 1.847 | 23.8 | 1.772 | |
| 17 | L03(main-body) | 2.087 | 2.282 | 1.720 | 50.2 | 1.772 | |
| 18 | | -7.901 | 1.440 | | | 1.772 | |
| 19 | L04(main-body) | Infinity | 3.544 | 1.5163 | 64.1 | 2.658 | |
| 20 | L05(main-body) | Infinity | 1.108 | 1.5163 | 64.1 | 2.658 | |
| 21 | | Infinity | 0.066 | | | 2.658 | |
| 22 | Image-plane | Infinity | 0.000 | | | 1.336 | |

FIG. 8

| (COMA AND SPHERICAL ABERRATION) | | | | | | |
|---|---|---|---|---|---|---|
| MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
| $R1 \div R2 > 3$ | $R1-(R2+d) > 0$ | $3 > Pw\_1st \div Pw\_2nd$ | $\nu d(-) - \nu d(+) > 0$ (AVERAGE) | $0 > 1/\nu d(-) - 1/\nu d(+)$ (AVERAGE) | $\nu d(-) > 35$ (AVERAGE) | $45 > \nu d(+)$ (AVERAGE) | $Num(-)-Num(+)=1$ |
| | | (COMPARISON BETWEEN FIRST AND SECOND DATA) | | | | | |
| 3.69 | 5.32 | 1.34 | 32.7 | −0.0330 | 51.6 | 18.9 | 1 |

FIG. 12

| # | | Radius | Thickness | Material | | Semi-Diameter | (n−1)/r surface_power |
|---|---|---|---|---|---|---|---|
| | | | | nd | νd | | |
| 0 | object | 45.3600 | 22.6800 | | | 43.568 | |
| 1 | L01 | 8.7159 | 0.9072 | 1.883 | 40.8 | 4.3092 | 0.21604 |
| 2 | | 2.3610 | 1.3040 | | | 2.0866 | −0.79755 |
| 3 | L02 | Infinity | 0.6418 | 1.595 | 67.7 | 2.7216 | 0 |
| 4 | | 1.5128 | 1.3550 | | | 1.2474 | −0.05451 |
| 5 | L03 | −1.2028 | 0.7938 | 1.595 | 67.7 | 0.9072 | −1.32629 |
| 6 | L04 | Infinity | 2.0058 | 1.883 | 40.8 | 1.2474 | 0 |
| 7 | | −2.9863 | 0.2268 | | | 1.2474 | 0.63054 |
| 8 | Stop(APERTURE) | Infinity | 0.2268 | | | 0.4777 | 0 |
| 9 | L05 | 7.8950 | 1.1701 | 1.516 | 64.1 | 1.2474 | 0.19206 |
| 10 | | Infinity | 0.2268 | | | 1.2474 | 0 |
| 11 | L06(CG) | Infinity | 0.9072 | 1.516 | 64.1 | 1.3608 | 0 |
| 12 | | Infinity | 0.2268 | | | 1.3608 | 0 |
| 13 | L01(main-body) | Infinity | 0.9072 | 1.516 | 64.1 | 1.5876 | 0 |
| 14 | | Infinity | 0.2268 | | | 1.5876 | |
| 15 | L02(main-body) | 5.4840 | 0.6804 | 1.847 | 23.8 | 1.8144 | |
| 16 | L03(main-body) | 2.1365 | 2.3360 | 1.720 | 50.2 | 1.8144 | |
| 17 | | −8.0900 | 1.4742 | | | 1.8144 | |
| 18 | L04(main-body) | Infinity | 3.6288 | 1.516 | 64.1 | 2.7216 | |
| 19 | L05(main-body) | Infinity | 1.1340 | 1.516 | 64.1 | 2.7216 | |
| 20 | | Infinity | 0.0680 | | | 2.7216 | |
| 21 | Image-plane | Infinity | 0.0000 | | | 1.3545 | |

FIG. 13

| | MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
|---|---|---|---|---|---|---|---|---|
| (COMA AND SPHERICAL ABERRATION) | $R1 \div R2 > 3$ | $R1-(R2+d) > 0$ | $3 > Pw\_1st \div Pw\_2nd$ (COMPARISON BETWEEN FIRST AND SECOND DATA) | $\nu d(-) - \nu d(+) > 0$ (AVERAGE) | $0 > 1/\nu d(-) - 1/\nu d(+)$ (AVERAGE) | $\nu d(-) > 35$ (AVERAGE) | $45 > \nu d(+)$ (AVERAGE) | $Num(-) - Num(+) = 1$ |
| | 3.69 | 5.45 | 1.26 | 18.0 | −0.0065 | 58.7 | 40.8 | 2 |

FIG. 17

| # | Radius | Thickness | Material nd | Material νd | Semi-Diameter | (n−1)/r surface_power |
|---|---|---|---|---|---|---|
| 0 | object | 22.7998 | | | 43.8067 | |
| 1 | 45.5996 | 0.9120 | 1.883 | 40.8 | 4.5600 | 0.21491 |
| 2 | 8.7620 | 1.3110 | | | 2.0976 | -0.79336 |
| 3 | 2.3735 | 0.6452 | | | 2.0976 | 0 |
| 4 | Infinity | 1.2480 | 1.6968 | 55.5 | 4.1040 | 0 |
| 5 | 2.7435 | 0.6840 | 1.6968 | 55.5 | 1.4820 | -0.61848 |
| 6 | -1.4148 | 2.5080 | 1.9229 | 18.9 | 1.0260 | -1.19933 |
| 7 | -5.8804 | 0.2280 | | | 1.3680 | 0 |
| 8 | -3.1851 | 1.1400 | 1.4875 | 70.2 | 1.3680 | 0.32699 |
| 9 | Infinity | 0.1140 | | | 1.3680 | 0.46701 |
| 10 | Stop(APERTURE) | 0.1140 | | | 0.4856 | 0 |
| 11 | L06(CG) Infinity | 0.9120 | 1.516 | 64.1 | 1.3680 | 0 |
| 12 | Infinity | 0.2280 | | | 1.3680 | 0 |
| 13 | L01(main-body) Infinity | 0.9120 | 1.516 | 64.1 | 1.5960 | 0 |
| 14 | Infinity | 0.2280 | | | 1.5950 | |
| 15 | L02(main-body) 5.5130 | 0.6840 | 1.847 | 23.8 | 1.8240 | |
| 16 | L03(main-body) 2.1477 | 2.3484 | 1.720 | 50.2 | 1.8240 | |
| 17 | -8.1327 | 1.4820 | | | 1.8240 | |
| 18 | L04(main-body) Infinity | 3.6480 | 1.516 | 64.1 | 2.7360 | |
| 19 | L05(main-body) Infinity | 1.1400 | 1.516 | 64.1 | 2.7360 | |
| 20 | Infinity | 0.0684 | | | 2.7360 | |
| 21 | Image-plane Infinity | 0.0000 | | | 1.3072 | |

FIG. 18

| | | (COMA AND SPHERICAL ABERRATION) | | | | |
|---|---|---|---|---|---|---|
| MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
| $R1 \div R2 > 3$ | $R1-(R2+d) > 0$ | $3 > Pw\_1st \div Pw\_2nd$ (COMPARISON BETWEEN FIRST AND SECOND DATA) | $\nu d(-) - \nu d(+) > 0$ (AVERAGE) | $0 > 1/\nu d(-) - 1/\nu d(+)$ (AVERAGE) | $\nu d(-) > 35$ (AVERAGE) | $45 > \nu d(+)$ (AVERAGE) | $Num(-)-Num(+)=1$ |
| 3.69 | 5.48 | 1.51 | 31.7 | −0.0134 | 50.6 | 44.6 | 1 |

FIG. 22

| # | | Radius | Thickness | Material nd | Material νd | Semi-Diameter | (n−1)/r surface_power |
|---|---|---|---|---|---|---|---|
| 0 | object | 41.6620 | 20.8310 | | | 38.8366 | |
| 1 | L01 | 8.0054 | 0.8332 | 1.8830 | 40.8 | 4.1662 | 0.23522 |
| 2 | | 2.3757 | 1.1978 | | | 1.9753 | −0.79261 |
| 3 | L02 | Infinity | 0.5895 | 1.6516 | 58.6 | 1.7531 | 0 |
| 4 | | 2.2528 | 1.3686 | | | 1.1974 | −0.73314 |
| 5 | L03 | −1.4805 | 0.6249 | 1.6968 | 55.5 | 0.7152 | −1.14612 |
| 6 | L04 | Infinity | 2.6454 | 1.9229 | 18.9 | 0.6948 | 0 |
| 7 | | −10.2133 | 0.2083 | | | 1.2499 | 0.18827 |
| 8 | L05 | 6.0631 | 1.2499 | 1.4875 | 70.2 | 1.2499 | 0.24534 |
| 9 | | −3.7991 | 0.1042 | | | 1.2499 | 0.39154 |
| 10 | Stop(APERTURE) | Infinity | 0.1042 | | | 0.4611 | 0 |
| 11 | L06(CG) | Infinity | 0.8332 | 1.5163 | 64.1 | 1.6665 | 0 |
| 12 | | Infinity | 0.2083 | | | 1.6665 | 0 |
| 13 | L01(main-body) | Infinity | 0.8332 | 1.8830 | 40.8 | 2.2914 | |
| 14 | L02(main-body) | Infinity | 1.8748 | 1.5891 | 61.1 | 2.2914 | |
| 15 | | −6.4156 | 0.1771 | | | 2.2914 | |
| 16 | L03(main-body) | 8.8801 | 2.4997 | 1.8160 | 46.6 | 2.7080 | |
| 17 | L04(main-body) | −5.2292 | 0.8332 | 1.9229 | 18.9 | 2.7080 | |
| 18 | | Infinity | 1.0416 | | | 2.4374 | |
| 19 | L05(main-body) | Infinity | 3.7496 | 1.5163 | 64.1 | 2.7080 | |
| 20 | L06(main-body) | Infinity | 0.6249 | 1.5163 | 64.1 | 1.2777 | |
| 21 | | Infinity | 0.0625 | | | 1.2985 | |
| 22 | Image-plane | Infinity | 0.000 | | | 1.3030 | |

FIG. 23

| | | (COMA AND SPHERICAL ABERRATION) | | | | |
|---|---|---|---|---|---|---|
| MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
| $R1 \div R2 > 3$ | $R1-(R2+d) > 0$ | $3 > Pw\_1st \div Pw\_2nd$ (COMPARISON BETWEEN FIRST AND SECOND DATA) | $\nu d(-) - \nu d(+) > 0$ (AVERAGE) | $0 > 1/\nu d(-) - 1/\nu d(+)$ (AVERAGE) | $\nu d(-) > 35$ (AVERAGE) | $45 > \nu d(+)$ (AVERAGE) | $Num(-) - Num(+) = 1$ |
| 3.37 | 4.80 | 1.45 | 7.0 | −0.0137 | 51.6 | 44.6 | 1 |

FIG. 27

| # | | Radius | Thickness | Material nd | Material νd | Semi-Diameter | (n-1)/r surface_power |
|---|---|---|---|---|---|---|---|
| 0 | object | 27.8202 | 13.9101 | | | 26.5737 | |
| 1 | L01 | 505695 | 0.4869 | 1.883 | 40.8 | 1.6692 | 0.33809 |
| 2 | | 0.8346 | 1.0290 | | | 0.7790 | -2.25615 |
| 3 | L02 | -1.2198 | 0.4869 | 1.516 | 64.1 | 0.4932 | -1.24307 |
| 4 | L03 | Infinity | 0.8624 | 1.785 | 25.7 | 0.7651 | 0 |
| 5 | Stop(APERTURE) | -4.4224 | 0.0210 | | | 0.7651 | 0.40357 |
| 6 | L04 | Infinity | 0.0209 | | | 0.2643 | 0 |
| 7 | | 3.1605 | 0.8624 | 1.516 | 64.1 | 0.7651 | 0.47977 |
| 8 | | -3.0775 | 0.1390 | | | 0.7651 | 0.49271 |
| 9 | L05(CG) | Infinity | 0.6955 | 1.883 | 40.8 | 0.8346 | 0 |
| 10 | | Infinity | 0.1391 | | | 0.8346 | 0 |
| 11 | L01(main-body) | Infinity | 0.5564 | 1.516 | 64.1 | 0.9737 | |
| 12 | | Infinity | 0.1391 | | | 0.9737 | |
| 13 | L02(main-body) | 3.3635 | 0.4173 | 1.847 | 23.8 | 1.1128 | |
| 14 | L03(main-body) | 1.3103 | 1.4327 | 1.720 | 50.2 | 1.1128 | |
| 15 | | -4.9617 | 0.9042 | | | 1.1128 | |
| 16 | L04(main-body) | Infinity | 2.2256 | 1.516 | 64.1 | 1.6692 | |
| 17 | L05(main-body) | Infinity | 0.6955 | 1.516 | 64.1 | 1.6692 | |
| 18 | | Infinity | 0.0120 | | | 1.6692 | |
| 19 | Image-plane | Infinity | 0.0000 | | | 1.2891 | |

FIG. 28

| (COMA AND SPHERICAL ABERRATION) | | | | | | |
|---|---|---|---|---|---|---|
| MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
| R1÷R2 > 3 | R1−(R2+d) > 0 | 3 > Pw_1st÷Pw_2nd | νd(−)−νd(+)>0 | 0>1/νd(−)−1/νd(+) | νd(−)>35 | 45>νd(+) | Num(−)−Num(+)=1 |
| | | (COMPARISON BETWEEN FIRST AND SECOND DATA) | (AVERAGE) | (AVERAGE) | (AVERAGE) | (AVERAGE) | |
| 6.67 | 4.25 | 1.81 | 26.8 | −0.0189 | 52.5 | 25.7 | 1 |

FIG. 32

| # | | Radius | Thickness | Material nd | νd | Semi-Diameter | (n−1)/r surface_power |
|---|---|---|---|---|---|---|---|
| 0 | object | Infinity | 6.782 | | | 99.944 | |
| 1 | L01 | Infinity | 0.543 | 1.8830 | 40.8 | 1.628 | 0 |
| 2 | | 1.398 | 0.866 | | | 1.017 | −1.34656 |
| 3 | L02 | −1.082 | 1.180 | 1.5163 | 64.1 | 0.678 | −1.40152 |
| 4 | L03 | Infinity | 0.963 | 1.9229 | 18.9 | 0.746 | 0 |
| 5 | | −12.936 | 0.020 | | | 0.746 | 0.14864 |
| 6 | Stop(APERTURE) | Infinity | 0.020 | | | 0.305 | 0 |
| 7 | L04 | 8.063 | 0.773 | 1.4970 | 81.5 | 0.746 | 0.18567 |
| 8 | | −1.992 | 0.136 | | | 0.746 | 0.75169 |
| 9 | L05(CG) | Infinity | 0.543 | 1.5163 | 64.1 | 1.085 | 0 |
| 10 | | Infinity | 0.136 | | | 0.648 | 0 |
| 11 | L01(main-body) | Infinity | 0.543 | 1.8830 | 40.8 | 1.400 | |
| 12 | L02(main-body) | Infinity | 1.221 | 1.5891 | 61.1 | 1.400 | |
| 13 | | −4.177 | 0.115 | | | 1.400 | |
| 14 | L03(main-body) | 5.782 | 1.628 | 1.8160 | 46.6 | 1.400 | |
| 15 | L04(main-body) | −3.405 | 0.543 | 1.9229 | 18.9 | 1.400 | |
| 16 | | Infinity | 0.678 | | | 0.928 | |
| 17 | L05(main-body) | Infinity | 2.442 | 1.5163 | 64.1 | 1.400 | |
| 18 | L06(main-body) | Infinity | 0.407 | 1.5163 | 64.1 | 1.400 | |
| 19 | Image-plane | Infinity | 0.000 | | | 1.400 | |

FIG. 33

| | | (COMA AND SPHERICAL ABERRATION) | | | | |
|---|---|---|---|---|---|---|
| MONOCHROMATIC ABERRATION CORRECTION | MENISCUS FORMING PROPERTIES | DISPERSION OF CONCAVE SURFACE (power_ratio) | LENS IN FRONT OF APERTURE | LENS IN FRONT OF APERTURE | LENS IN FRONT OF APERTURE | LENS IN FRONT OF APERTURE | MINIMUM LENS CONFIGURATION |
| $R1 \div R2 > 3$ | $R1-(R2+d) > 0$ | $3 > Pw\_1st \div Pw\_2nd$ | $\nu d(-) - \nu d(+) > 0$ (AVERAGE) | $0 > 1/\nu d(-) - 1/\nu d(+)$ (AVERAGE) | $\nu d(-) > 35$ (AVERAGE) | $45 > \nu d(+)$ (AVERAGE) | $Num(-) - Num(+) = 1$ |
| | | (COMPARISON BETWEEN FIRST AND SECOND DATA) | | | | | |
| Infinity | Infinity | 1.04 | 33.6 | −0.0329 | 52.5 | 18.9 | 1 |

ENDOSCOPE SYSTEM AND OPTICAL ADAPTOR FOR ENDOSCOPE

CROSS REFERENCE TO RELATED APPLICATION

This application claims benefit of Japanese Application No. 2019-45765 filed in Japan on Mar. 13, 2019, the contents of which are incorporated by this reference.

BACKGROUND OF THE INVENTION

1. Field of the Invention

The present invention relates to an endoscope system and an optical adaptor for endoscope.

2. Description of Related Art

In the related art, an endoscope has been used in an industrial field and a medical field. An endoscope includes an elongated insertion portion, and the insertion portion is inserted into a subject or object. An observation window is provided in a distal end portion of the insertion portion, and an image of an observation site incident through the observation window is displayed as an endoscopic image by a display apparatus.

A bending portion may be provided in a proximal end of the distal end portion of the insertion portion. The insertion portion of the endoscope is disposed in a narrow space. Therefore, it is preferable that the angle of view of the endoscope system is wider.

Japanese Patent Application Laid-Open Publication No. 2016-151629 discloses an endoscope including a wide-angle objective optical system. In addition, Japanese Patent Application Laid-Open Publication No. H01-269909 discloses an endoscope in which the angle of view of an objective optical system is widened by an optical adaptor attached to the endoscope.

SUMMARY OF THE INVENTION

An endoscope system according to one aspect of the present invention includes a removable adaptor and a main body optical system, in which the adaptor includes an aperture and includes a first group optical system having a negative combined focal length as a whole and a second group optical system having a positive combined focal length as a whole in order from an object side, the main body optical system includes an imaging lens configured to form an image of a light flux on an image pickup device, the light flux being transmitted through the adaptor from the object, the first group optical system includes a lens having an Abbe number of 35 or higher, and the second group optical system includes a lens having an Abbe number of 45 or lower.

An optical adaptor for endoscope according to another aspect of the present invention is removable from a distal end portion of an insertion portion of an endoscope, the optical adaptor including: an aperture; a first group optical system having a negative combined focal length as a whole; and a second group optical system having a positive combined focal length as a whole, in which the first group optical system and the second group optical system are provided in order from an object side, the first group optical system includes a lens having an Abbe number of 35 or higher, and the second group optical system includes a lens having an Abbe number of 45 or lower.

BRIEF DESCRIPTION OF THE DRAWINGS

FIG. 7 is a table representing lens data of the objective optical system in the first embodiment of the present invention;

FIG. 8 is a table representing various numerical data of the objective optical system in the first embodiment of the present invention;

FIG. 12 is a table representing lens data of the objective optical system in the second embodiment of the present invention;

FIG. 13 is a table representing various numerical data of the objective optical system in the second embodiment of the present invention;

FIG. 17 is a table representing lens data of the objective optical system in the third embodiment of the present invention;

FIG. 18 is a table representing various numerical data of the objective optical system in the third embodiment of the present invention;

FIG. 22 is a table representing lens data of the objective optical system in the fourth embodiment of the present invention;

FIG. 23 is a table representing various numerical data of the objective optical system in the fourth embodiment of the present invention;

FIG. 27 is a table representing lens data of the objective optical system in the fifth embodiment of the present invention;

FIG. 28 is a table representing various numerical data of the objective optical system in the fifth embodiment of the present invention;

FIG. 32 is a table representing lens data of the objective optical system in the sixth embodiment of the present invention;

FIG. 33 is a table representing various numerical data of the objective optical system in the sixth embodiment of the present invention;

DETAILED DESCRIPTION OF THE PREFERRED EMBODIMENT(S)

Embodiments of the present invention will be described below with reference to the drawings.

First Embodiment

Configuration of Endoscope Apparatus

Figure 1:
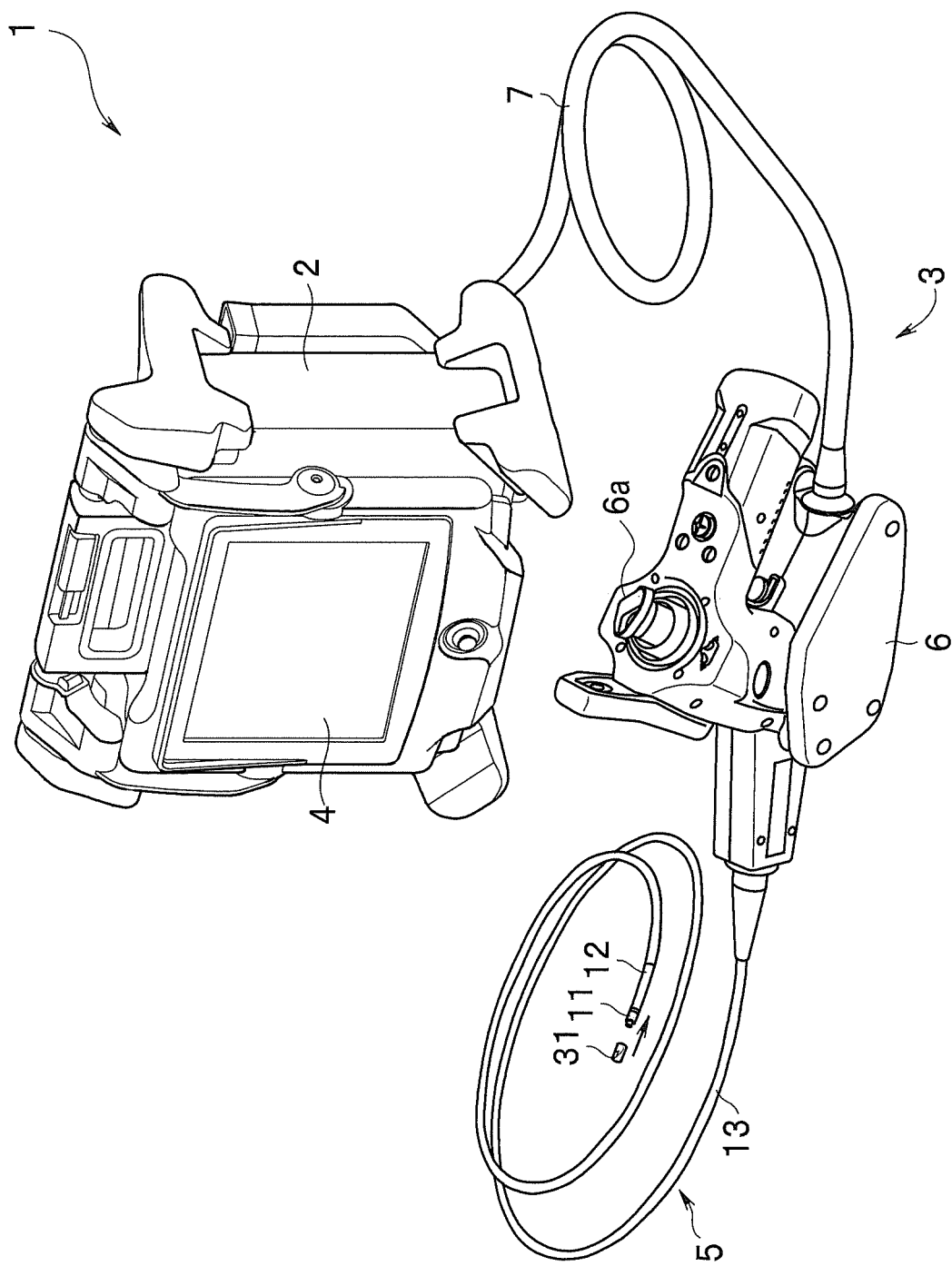
FIG. 1 is a diagram illustrating a configuration of an endoscope apparatus in a first embodiment of the present invention.

FIG. 1 is a diagram illustrating a configuration of an endoscope apparatus according to the present embodiment. As illustrated in FIG. 1, an endoscope apparatus 1 is an endoscope system including an apparatus body 2 having a function of a video processor or the like and an endoscope 3 connected to the apparatus body 2. The apparatus body 2 includes a display portion 4 such as a liquid crystal panel (LCD) on which an endoscopic image, an operation menu, and the like are displayed. The display portion 4 may be provided with a touch panel. Note that the display portion 4 may be configured separately from the apparatus body 2, and image data, operation signals, and the like may be transmitted and received wirelessly between the display portion 4 and the apparatus body 2.

The endoscope 3 includes an insertion portion 5 as an endoscope insertion portion configured to be inserted into a subject or object, an operation portion 6 provided at a proximal end of the insertion portion 5, and a universal cord 7 extending from the operation portion 6. The endoscope 3 is removably mounted on the apparatus body 2 via the universal cord 7.

The insertion portion 5 includes a distal end portion 11, a bending portion 12, and a longitudinal flexible portion 13 in order from its distal end side. The bending portion 12 is consecutively provided at a proximal end of the distal end portion 11 and is configured to be bendable, for example, in vertical and horizontal directions. The flexible portion 13 is consecutively provided at a proximal end of the bending portion 12 and has flexibility. A light guide 40 (FIG. 3) that guides illumination light is inserted into the insertion portion 5. A light source is embedded in the apparatus body 2, illumination light of the light source is emitted to a proximal end surface of the light guide 40, and the illumination light is guided to a distal end surface of the light guide 40.

An image pickup device 23 (FIG. 2) such as a CMOS image sensor is embedded in the distal end portion 11 of the insertion portion 5. The image pickup device 23 receives incident light incident on an observation window (not illustrated) provided in the distal end portion 11 of the insertion portion 5.

As indicated by an arrow, an optical adaptor 31 can be removably mounted on the distal end portion 11. The endoscope 3 can be used as a wide-angle endoscope by mounting the wide-angle optical adaptor 31 on the distal end portion 11.

The operation portion 6 is provided with a bending joystick 6a configured to bend the bending portion 12 in vertical and horizontal directions. A user can bend the bending portion 12 in a desired direction by performing an operation for inclining the bending joystick 6a. The operation portion 6 is provided with buttons configured to indicate an endoscope function, for example, various operation buttons such as a freeze button, a bending lock button, and a recording instruction button in addition to the bending joystick 6a.

Note that in a configuration in which the display portion 4 is provided with a touch panel, the user may operate the touch panel to indicate various operations of the endoscope apparatus 1.

An endoscopic image of a subject or object obtained by the image pickup device 23 (FIG. 2) in the image pickup unit provided in the distal end portion 11 performing image pickup is displayed on the display portion 4 in the apparatus body 2. Various circuits such as a controller (not illustrated) configured to perform image processing and various controls or a recording device configured to record a processed image in a memory (not illustrated) are provided in the apparatus body 2.

Configuration of Optical Adaptor

Figure 2:
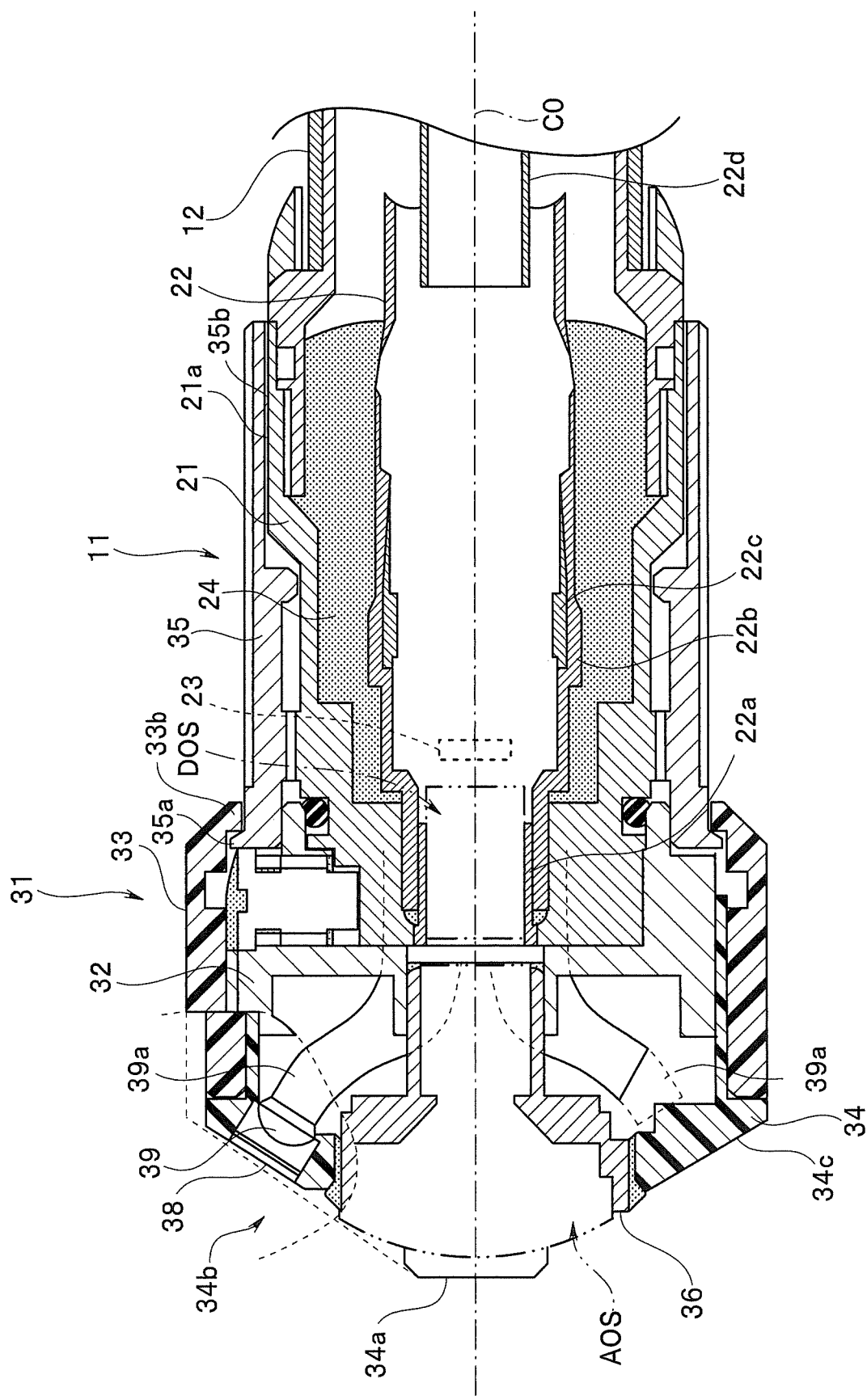
FIG. 2 is a sectional view taken along a longitudinal axis of an insertion portion illustrating a distal end portion of the insertion portion on which an optical adaptor is mounted in the first embodiment of the present invention.
Figure 3:
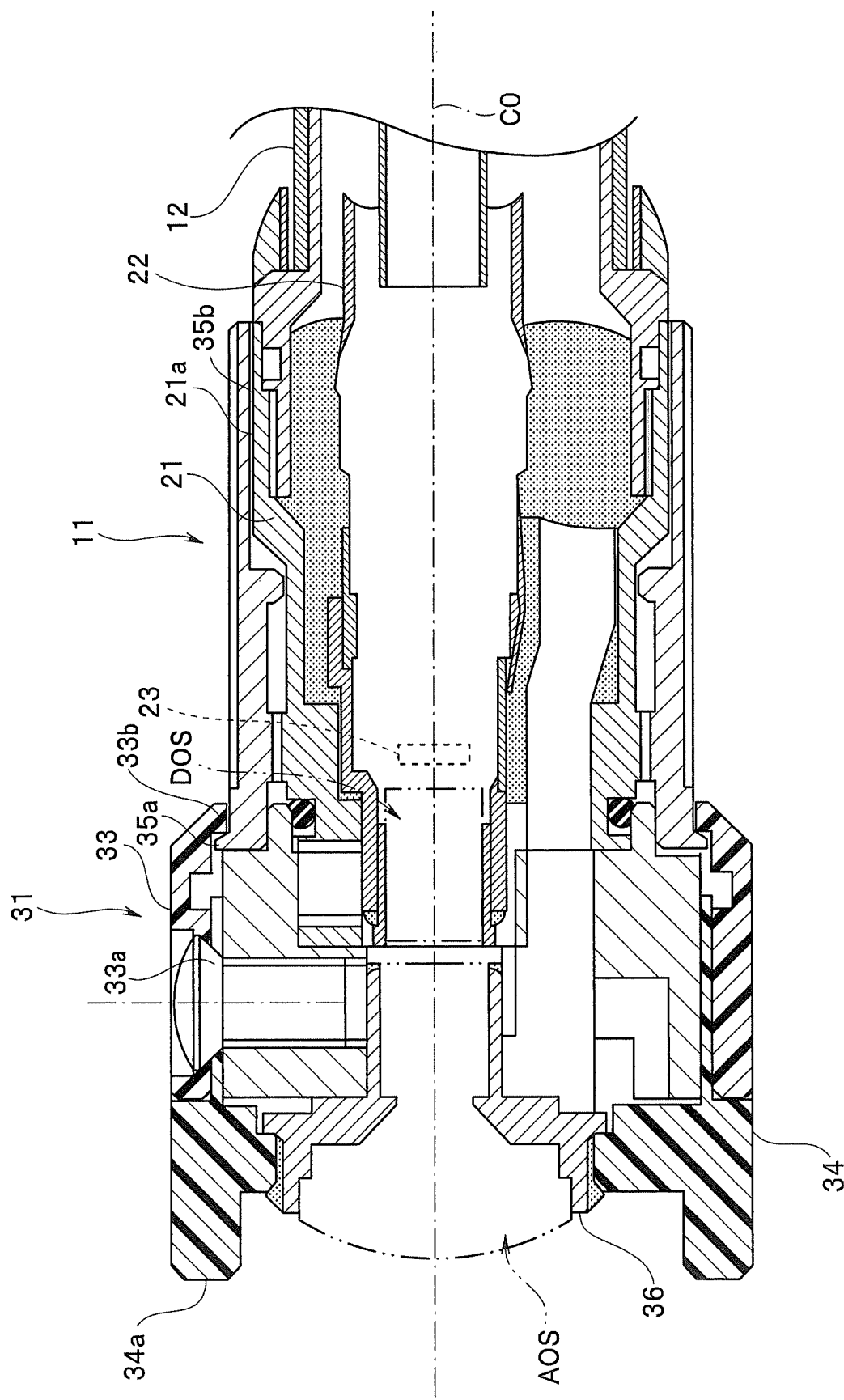
FIG. 3 is a sectional view taken along the longitudinal axis of the insertion portion illustrating the distal end portion of the insertion portion on which the optical adaptor is mounted in the first embodiment of the present invention.
Figure 4:
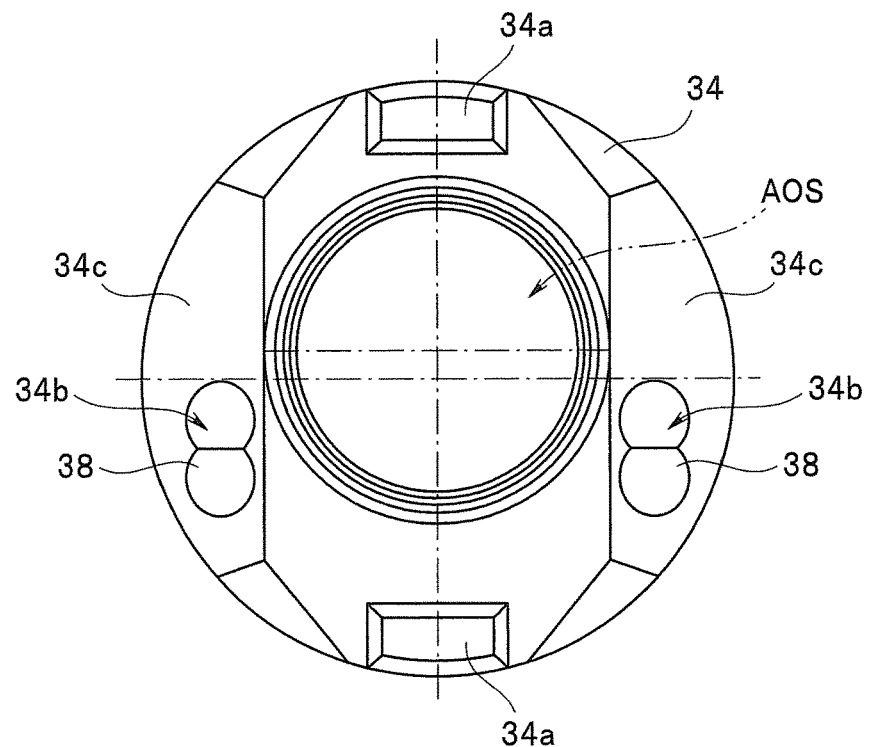
FIG. 4 is a front view illustrating the optical adaptor when seen from the object side in the first embodiment of the present invention.

FIGS. 2 and 3 are sectional views taken along a longitudinal axis of the insertion portion illustrating the distal end portion of the insertion portion on which the optical adaptor is mounted. FIG. 3 illustrates a section perpendicular to a section of FIG. 2. FIG. 4 is a front view illustrating the optical adaptor when seen from an object side.

As illustrated in FIGS. 2, 3, and 4, the distal end portion 11 of the insertion portion 5 includes a distal end rigid member 21 formed of metal such as stainless steel. The image pickup unit 22 is embedded in the cylindrical distal end rigid member 21. The image pickup unit 22 includes an optical system DOS (indicated by a two-dot chain line) including a plurality of lenses and an image pickup device 23. The image pickup unit 22 is fitted to a fitting hole formed in the distal end rigid member 21 and is fixed thereto through an adhesive 24. The distal end rigid member 21 includes a screw portion 21a in which a male screw is formed on a proximal end side outer peripheral surface.

The image pickup unit 22 includes a cylindrical frame member 22a configured to fix the optical system DOS, cylindrical frame members 22b and 22c configured to fix the frame member 22a and the image pickup device 23, and a cable 22d into which various signal lines extending from the image pickup device 23 are inserted. Here, the image pickup unit 22 is formed as one unit and is inserted from a proximal end of the distal end rigid member 21 into the fitting hole formed in the distal end rigid member 21 to be fixed. The optical system DOS of the image pickup unit 22 includes an imaging lens configured to form an image of a light flux on the image pickup device 23, the light flux being transmitted through the optical adaptor 31 from an object.

The optical adaptor 31 is removably mounted on the distal end portion 11 of the insertion portion 5. Accordingly, the endoscope apparatus 1 is an endoscope system including the removable optical adaptor 31 and the optical system DOS as a main body optical system. Therefore, the optical adaptor 31 includes a main body member 32, a cylindrical member 33, a distal end cover 34, an attachment ring 35, an optical system AOS (indicated by a two-dot chain line) including a plurality of lenses, and a frame member 36. The cylindrical main body member 32 is a rigid member formed of metal such as stainless steel. The distal end cover 34 is fixed to the main body member 32 through a screw, an adhesive, or the like so as to protect a distal end surface of the main body member 32. The distal end cover 34 has an opening for allowing light to be incident on the optical system AOS. The distal end cover 34 includes two protrusion portions 34a protruding toward the distal end side in a periphery portion. Each of the protrusion portions 34a is provided, for example, to protect a surface of the optical system AOS from being scratched when a member in a subject or object collides with the surface of the optical system AOS. The frame member 36 is a cylindrical member configured to fix the optical system AOS. The optical system AOS is provided in the frame member 36.

The cylindrical member 33 is fixed to the main body member 32 through a screw 33a so as to cover the main body member 32. The cylindrical member 33 includes an inward flange 33b in a proximal end portion. The frame member 36 is fixed into the cylindrical member 33 through an adhesive or the like.

A female screw portion is formed on a distal end side inner peripheral surface of the cylindrical member 33, and a male screw portion is formed on a proximal end side outer peripheral surface of the distal end cover 34. By screwing the female screw portion of the cylindrical member 33 and the male screw portion of the distal end cover 34 together, the distal end cover 34 is fixed to the cylindrical member 33.

The attachment ring 35 is a cylindrical member, and the outer diameter thereof is less than the inner diameter of the cylindrical member 33. The attachment ring 35 includes an outward flange 35a in a distal end portion and includes a screw portion 35b in which a female screw is formed on an inner peripheral surface of a proximal end portion. The outward flange 35a can engage with the inward flange 33b of the cylindrical member 33.

When the attachment ring 35 rotates, the attachment ring 35 moves relative to the distal end rigid member 21 along a center axis of the distal end rigid member 21 due to the screwing between the screw portion 21a and the screw portion 35b. When the attachment ring 35 rotates in a first direction, the attachment ring 35 moves in a proximal end direction of the distal end rigid member 21. When the attachment ring 35 rotates in a direction opposite to the first direction, the attachment ring 35 moves in a distal end direction of the distal end rigid member 21.

When the attachment ring 35 moves in the proximal end direction, the outward flange 35a pulls the inward flange 33b such that the inward flange 33b moves in the proximal end direction. Therefore, the optical adaptor 31 is fixed to the distal end portion 11 of the insertion portion 5. When the attachment ring 35 moves in the distal end direction, the screwing between the screw portion 21a and the screw portion 35b is released. In this case, the user can remove the optical adaptor 31 from the distal end portion 11 of the insertion portion 5.

The optical adaptor 31 includes two illumination windows 34b. A cover glass 38 is provided in each of the illumination windows 34b, and an illumination lens 39 is provided in back of the cover glass 38. A distal end surface of a light guide 39a formed of an optical fiber bundle is disposed in back of each of the illumination lenses 39. When the optical adaptor 31 is mounted on the distal end portion 11, proximal end surfaces of the two light guides 39a are disposed at positions facing the distal end surface of the light guide 40 inserted into the distal end portion 11.

To allow a wide range of area to be illuminated, the two illumination windows 34b are disposed on an inclined surface 34c of the distal end cover 34 that is inclined by a predetermined angle θ, here, by 30 degrees, with respect to a surface perpendicular to an optical axis C0 of an objective optical system.

The objective optical system is a wide-angle optical system configured with the optical systems DOS and AOS. In general, the wide-angle optical system has an angle of view of 140 degrees or more. Here, the objective optical system configured with the optical systems DOS and AOS has an angle of view of 220 degrees which is more than 180 degrees.

Figure 5:
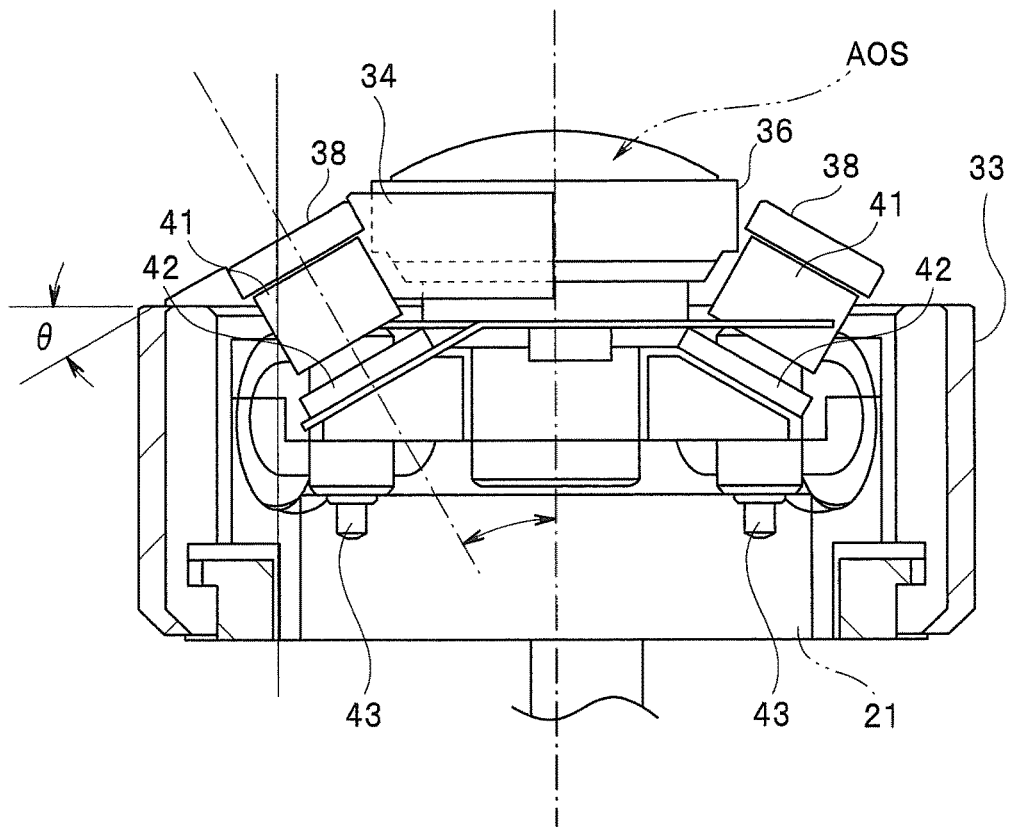
FIG. 5 is a sectional view taken along an optical axis of the optical adaptor including a light emitting element in the first embodiment of the present invention.

For the above-described illumination, the illumination light guided by the light guide is emitted from the illumination windows 34b. However, for the illumination, a light emitting element may also be used. FIG. 5 is a sectional view taken along the optical axis C0 of the optical adaptor including the light emitting element.

In this case, two quadrangular prisms 41 configuring the illumination optical system are provided in back of the two cover glasses 38. A light emitting element 42 is provided in back of each of the quadrangular prisms 41. The light emitting element 42 is, for example, a light emitting diode (LED). A signal line (not illustrated) extending from each of the light emitting elements 42 is connected to a contact pin 43 provided in a proximal end portion of the optical adaptor 31.

A signal line (not illustrated) that supplies a driving current from the apparatus body 2 is inserted into the insertion portion 5. When the optical adaptor 31 is attached to the distal end portion 11, two contact pins 43 come into contact with two contacts (not illustrated) provided in the distal end portion 11 and are electrically connected to the signal line inserted into the insertion portion 5.

Configuration of Optical System

Next, a configuration of the objective optical system will be described.

Figure 6:
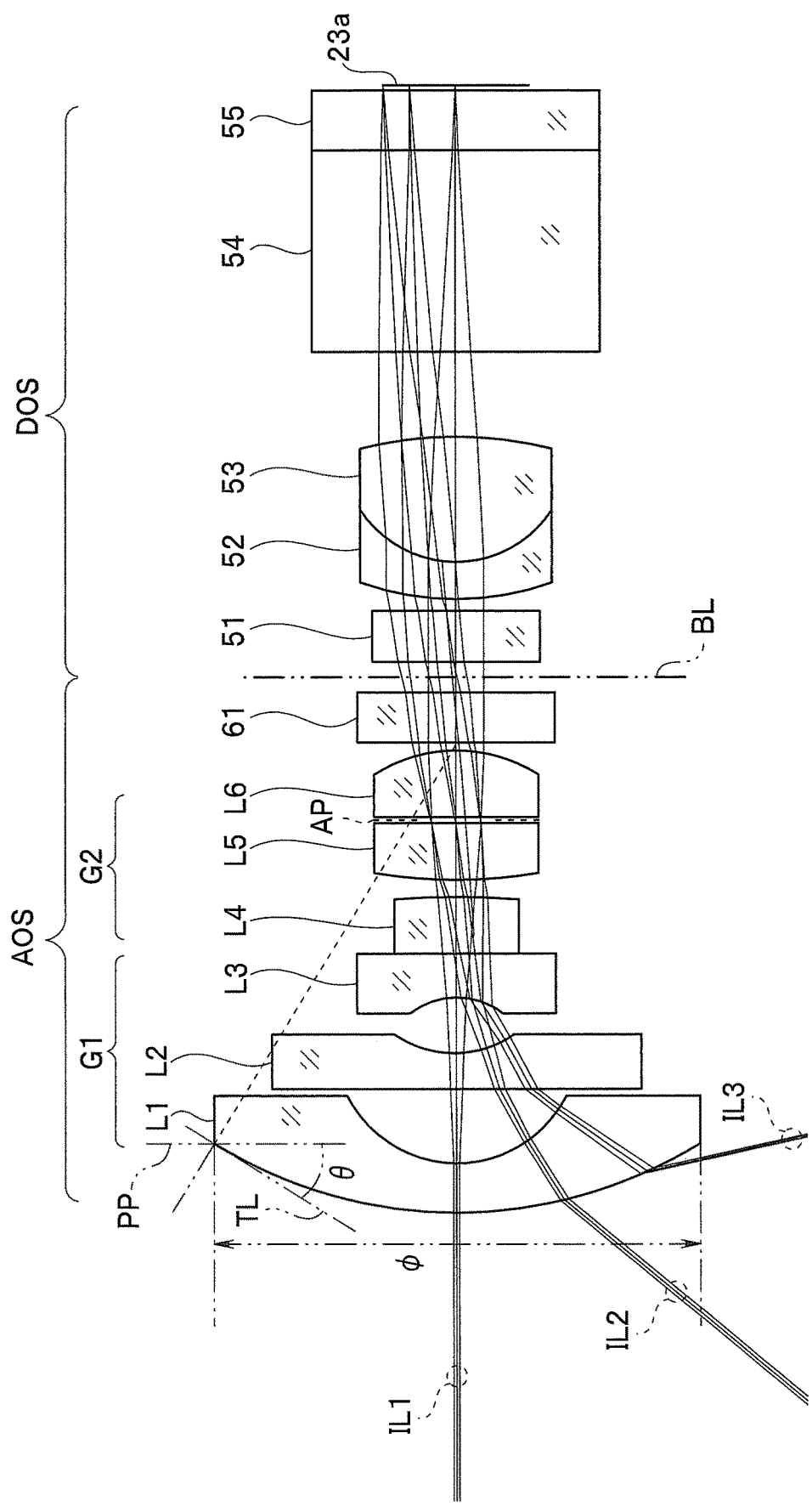
FIG. 6 is a diagram illustrating a configuration of an objective optical system in the first embodiment of the present invention.

FIG. 6 is a diagram illustrating the configuration of the objective optical system in the present embodiment. In FIG. 6, a two-dot chain line BL indicates a boundary between the optical system AOS of the optical adaptor 31 and the optical system DOS of the distal end portion 11. The optical system DOS of the distal end portion 11 includes a cover glass 51, lenses 52 and 53, a protective glass 54, and a cover glass 55 in order from the distal end side.

The cover glass 51 is a parallel plate. The lens 52 is a meniscus lens. The lens 53 is a biconvex lens. The protective glass 54 is also a parallel plate. The cover glass 55 is fixed to a light receiving surface 23a side of the image pickup device 23.

The optical system AOS of the optical adaptor 31 includes lenses L1 to L6 and a cover glass 61 in order from the distal end side, that is, the object side. The lenses L1, L2, and L3 are a concave lens group G1, and the lenses L4, L5, and L6 are a convex lens group G2.

The lens L1 is a meniscus lens. The lens L2 is a plano-concave lens. The lens L3 is a concave flat lens. The lens L4 is a plano-convex lens. The lens L5 is a convex flat lens. The lens L6 is a plano-convex lens. An aperture AP is disposed between the lenses L5 and L6. In other words, the first group optical system includes a meniscus lens (L1) disposed to be convex on the object side and a lens (L3) having a concave surface on the object side.

Light emitted from the cover glass 61 of the optical adaptor 31 is parallel light and is incident on the optical system DOS of the distal end portion. In other words, the lenses L1 to L6 and the aperture AP configure a substantially afocal optical system.

As described above, the optical adaptor 31 further includes the aperture AP and includes a first group optical system (concave lens group) having a negative combined focal length f as a whole and a second group optical system (convex lens group) having a positive combined focal length f as a whole in order from the object side.

The angle of view of the first group optical system (concave lens group) on the object side in the objective optical system is a wide angle which is 140 degrees or more, and the range of the ultra-wide angle of view is set in a range of 200 degrees to 220 degrees.

Here, in order to set the angle of view of the objective optical system to 220 degrees, as illustrated in FIG. 6, it is necessary that a tangential line TL of a periphery portion of the lens L1 along the optical axis of the objective optical system has an angle θ of 20 degrees or more with respect to a surface PP perpendicular to the optical axis of the objective optical system. When the outer diameter of the lens L1 is represented by φ and the curvature radius of a spherical surface of the lens L1 on the distal end side is represented by R, the following expression is satisfied.

$$(\phi/2 \tan\theta) \geq R \quad (1)$$

When the angle of view of the concave lens group G1 is set, the curvature radius R and the outer diameter φ are determined by Expression (1). Accordingly, the optical system AOS of the elongated optical adaptor 31 can be designed based on Expression (1).

The angle of view of the first group optical system on the object side is 220 degrees.

FIG. 6 illustrates a light ray IL1 at 0 degrees, a light ray IL2 at 50 degrees, and a light ray IL3 at 100 degrees with respect to the optical axis of the objective optical system. Here, an F number of the objective optical system is 5.0. In the optical adaptor 31, the optical system AOS has a six-lens configuration, in which three concave lenses and three convex lenses are used. The number of lenses on the object side with respect to the aperture AP is 5, in which the number of concave lenses is 3 and the number of convex lenses is 2.

When a principal ray is traced from the image side of the objective optical system, the angle of the principal ray decreases toward the object side relative to the aperture AP by the principal ray being condensed by the convex lenses and subsequently rapidly increases by the principal ray being diverged by the concave lenses. Therefore, by decreasing the height of the principal ray, a reduction in the diameter of the optical adaptor 31 can be realized.

The performance of the objective lens according to the present embodiment will be described. FIG. 7 is a table representing lens data of the objective optical system in FIG. 6. FIG. 7 illustrates the curvature radius (mm), the thickness (mm), the material, the refractive index (nd), the Abbe number (vd), the semi-diameter, and the surface power of each of the lenses. In FIG. 7, the lenses L1, L2, L3, L4, L5, and L6 and the cover glass 61 in the optical adaptor 31 are represented by L01, L02, L03, L04, L05, and L06. The cover glass 61, the lenses 51, 52, and 53, the protective glass 54, and the cover glass 55 in the distal end portion 11 are represented by L01 (main body), L02 (main body), L03 (main body), L04 (main body), L05 (main body), and L06 (main body).

FIG. 8 is a table representing various numerical data of the objective optical system in FIG. 6. FIG. 8 illustrates various numerical data of the objective optical system when the curvature radii of the meniscus lens are represented by R1 and R2 and the thickness thereof is represented by d.

As illustrated in FIG. 7, the first group optical system (concave lens group G1) includes a lens having an Abbe number v1 of 35 or higher (having a low dispersion), and the second group optical system includes a lens having an Abbe number v2 of 45 or lower (having a high dispersion).

Figure 9:
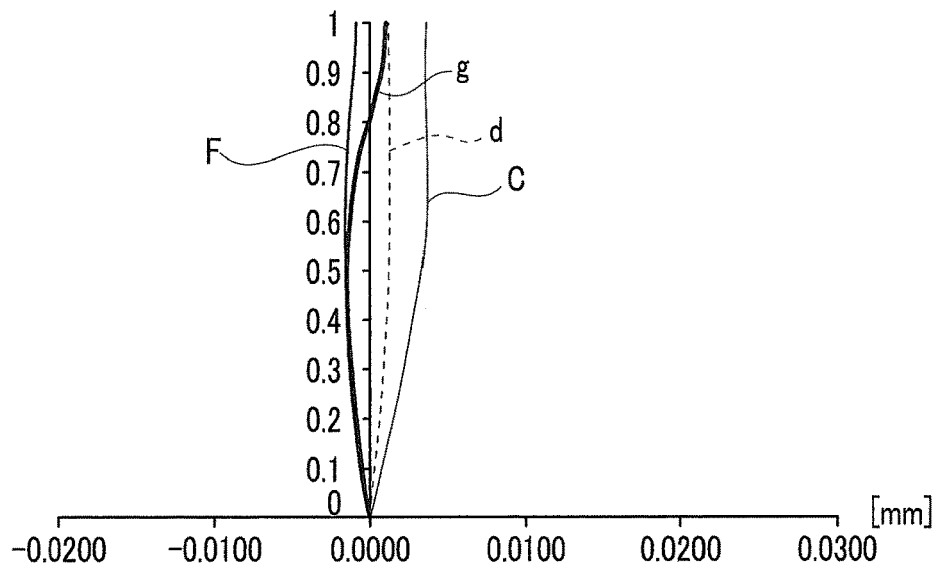
FIG. 9 is a graph illustrating lateral chromatic aberration of the objective optical system in the first embodiment of the present invention.

FIG. 9 is a graph illustrating lateral chromatic aberration of the objective optical system in FIG. 6. FIG. 9 illustrates the amount of shift (lateral chromatic aberration) on the image plane with respect to an e-ray (light having a wavelength of 0.546 µm). In FIG. 9, g represents the amount of shift of a g-ray having a wavelength of 0.436 µm, F represents the amount of shift of an F-ray having a wavelength of 0.486 µm, d represents the amount of shift of a d-ray having a wavelength of 0.588 µm, and C represents the amount of shift of a C-ray having a wavelength of 0.656 µm.

Figure 10:
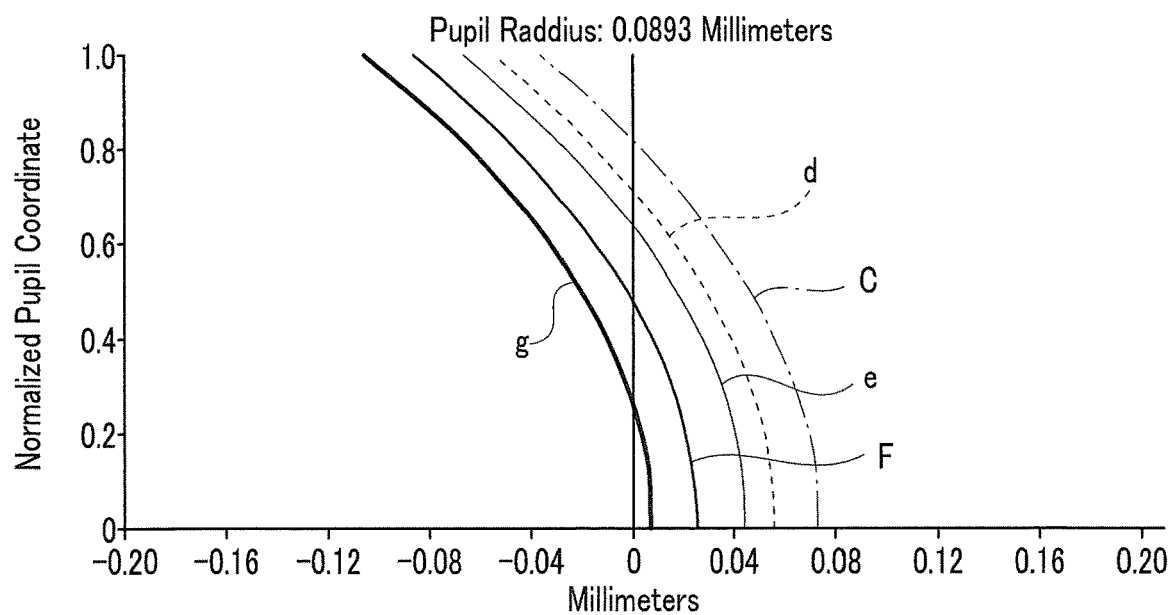
FIG. 10 is a graph illustrating an axial chromatic aberration of the objective optical system in the first embodiment of the present invention.

The amount of shift is 5 µm at most, and the chromatic aberration is favorably corrected at a level of a pixel size (several micrometers). FIG. 10 is a graph illustrating an axial chromatic aberration of the objective optical system in FIG. 6.

As illustrated in FIG. 8, the first lens L1 of a distal end of the first group optical system toward the object side is a meniscus lens, and a ratio of the curvature radius R1 of the meniscus lens on the distal end side to the curvature radius R2 of the meniscus lens on the proximal end side is 3.69, which is higher than or equal to 3.

Further, as illustrated in FIG. 8, the curvature radius R1 of the spherical surface of the lens L1 on the distal end side is more than a value obtained by adding the thickness d of the lens L1 on the optical axis to the curvature radius R2 of the spherical surface of the lens L1 on the proximal end side. In other words, the sum of the curvature radius R2 of the Lens L1 on the proximal end side and the thickness d of the lens L1 along the optical axis is less than the curvature radius R1 of the lens L1 on the distal end side. In other words, |R1|>(|R2|+d). Here, 8.51>(2.30+0.88).

In addition, a ratio (max (L1, L2, L3)/min (L1, L2, L3)) of a maximum power to a minimum power in the three lenses L1, L2, and L3 of the concave lens group G1 is 3 or lower. Here, the ratio is 1.34.

Accordingly, with the objective optical system according to the present embodiment, the following operation and effects can be obtained.

1) Since the convex lens group G2 is on the image side of the concave lens group G1, the light flux diameter of a marginal light ray in the optical adaptor 31 can be reduced.

2) As the aperture AP in the optical adaptor 31 approaches the object side of the objective optical system, the outer diameter of the distal end portion 11 can be reduced while maintaining the angle of view of the objective optical system.

3) As illustrated in FIG. 7, by using a glass having a low dispersion (having a high Abbe number vd) as the lens L6 that is a convex lens on the image side relative to the aperture AP and using a glass having a significantly high dispersion as the two lenses L4 and L5 that are convex lenses in front of the aperture AP, the lateral chromatic aberration is corrected.

As described above, the Abbe numbers of the lenses L1, L2, and L3 in the first group optical system are higher than or equal to 35 and specifically are 40.8, 55.5, and 58.6, respectively. The Abbe numbers of the lenses L4 and L5 in the second group optical system are lower than or equal to 45 and specifically are 18.9 and 18.9, respectively.

In particular, as illustrated in FIG. 8, the Abbe numbers of the respective lenses L1, L2, and L3 as the lenses on the object side relative to the aperture AP are higher than the Abbe numbers of the respective lenses L4 and L5 as the lenses on the object side relative to the aperture AP by 20 or higher. Here, the difference in Abbe number is 32.7.

The axial chromatic aberration is corrected by using the lens L6 that is the convex lens formed of glass having a low dispersion. In other words, the Abbe number of the lens L6 in back of (image side) the aperture AP is higher than the Abbe number of the second group optical system.

4) In addition, the lens L1 of the distal end is formed of a scratch-resistant hard glass having a high refractive index (nd) and a medium dispersion. Since the lens L1 has a high power, the chromatic aberration is generated but is corrected by the lenses L4 and L5 having a low Abbe number.

5) Further, in the lenses L2 and L3 having concave surfaces facing each other, the generation of spherical aberration and chromatic aberration such as lateral chromatic aberration is suppressed using a glass having a medium refractive index and a medium dispersion. As a whole, the monochromatic aberration (spherical aberration) and the chromatic aberration are corrected.

As described above, the present embodiment can provide an optical adaptor for endoscope that can suppress an increase in the number of lenses in the optical adaptor while favorably correcting chromatic aberration when mounted on the distal end portion of the insertion portion.

Second Embodiment

The optical adaptor 31 according to the first embodiment includes six lenses. The optical adaptor 31 according to a second embodiment includes five lenses, the number of which is less than the number of lenses in the first embodiment.

The configurations of the endoscope apparatus and the optical adaptor according to the present embodiment are the same as those of the endoscope apparatus and the optical adaptor according to the first embodiment except for the objective optical system. Therefore, the same components are represented by the same reference numerals, the description thereof will not be repeated, and only the configuration of the objective optical system will be described.

Figure 11:
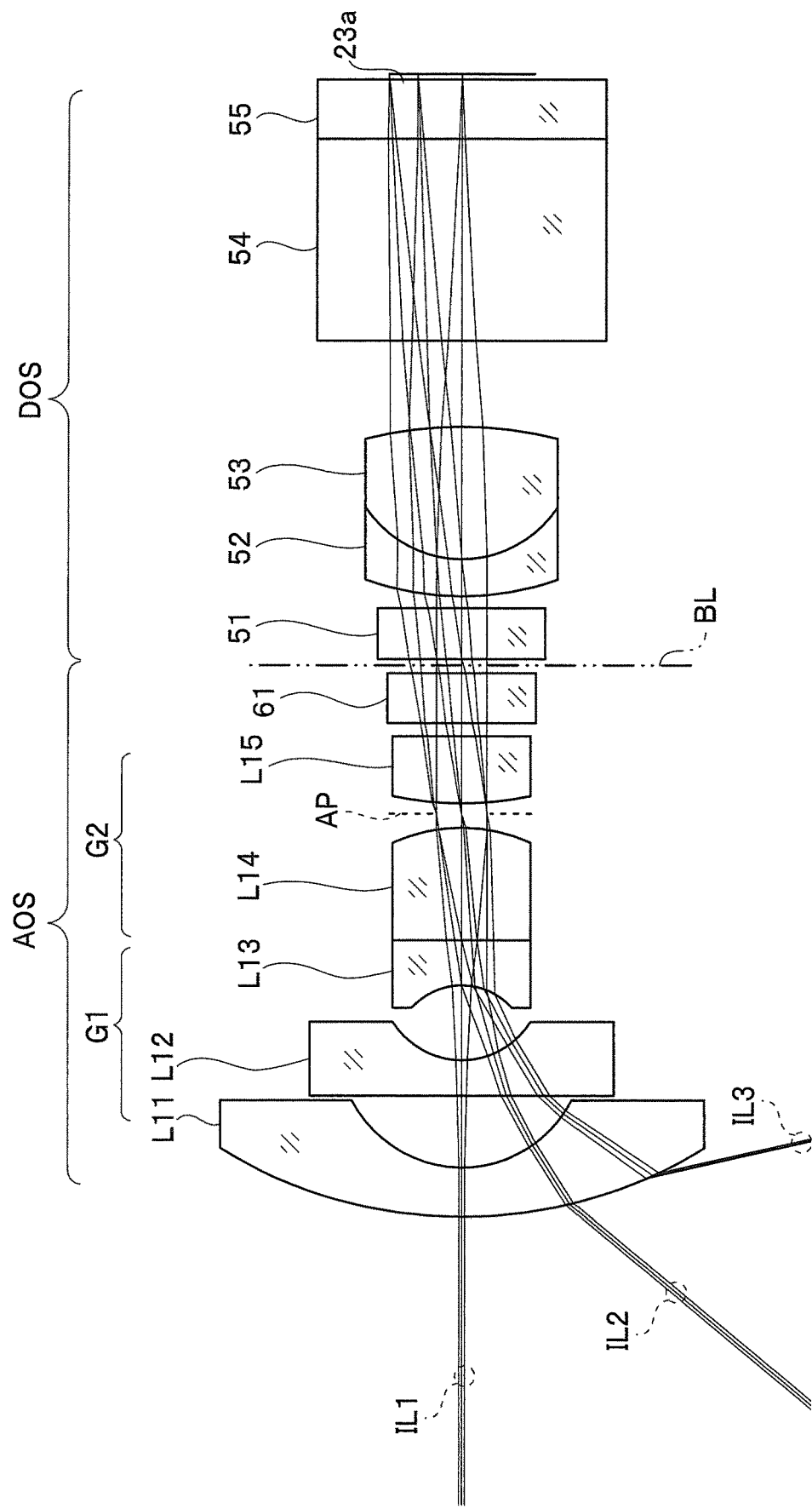
FIG. 11 is a diagram illustrating a configuration of an objective optical system in a second embodiment of the present invention.

FIG. 11 is a diagram illustrating the configuration of the objective optical system in the present embodiment. The optical system AOS of the optical adaptor 31 includes lenses L11 to L15 and the cover glass 61 in order from the distal end side. The lenses L11, L12, and L13 are a concave lens group G1, and the lenses L14 and L15 are a convex lens group G2. The angle of view of the concave lens group G1 is 220 degrees.

The lens L11 is a meniscus lens. The lens L12 is a plano-concave lens. The lens L13 is a concave flat lens. The lens L14 is a plano-convex lens. The lens L15 is a convex flat lens. The aperture AP is disposed between the lenses L14 and L15. In other words, the first group optical system includes a meniscus lens (L11) disposed to be convex on the object side and the lens (L13) having a concave surface on the object side.

Light emitted from the optical adaptor 31 is parallel light and is incident on the optical system DOS of the distal end portion 11. In other words, the lenses L11 to L15 and the aperture AP configure an afocal optical system.

As described above, the optical adaptor 31 further includes the aperture AP and includes a first group optical system having a negative combined focal length f as a whole and a second group optical system having a positive combined focal length f as a whole in order from the object side.

FIG. 11 illustrates a light ray IL1 at 0 degrees, a light ray IL2 at 50 degrees, and a light ray IL3 at 100 degrees with respect to the optical axis of the objective optical system. Here, an F number of the objective optical system is 6.0. In the optical adaptor 31, the optical system AOS has a five-lens configuration, in which three concave lenses and two convex lenses are used. The number of lenses on the object side with respect to the aperture AP is 4, in which the number of concave lenses is 3 and the number of convex lenses is 1.

When a principal ray is traced from the image side of the objective optical system, the angle of the principal ray decreases toward the front of the aperture AP, that is, the object side relative to the aperture AP and subsequently rapidly increases. Therefore, by decreasing the height of the principal ray, a reduction in the diameter of the optical adaptor 31 can be realized.

The performance of the objective lens according to the present embodiment will be described. FIG. 12 is a table representing lens data of the objective optical system in FIG. 11. FIG. 12 is a table representing the same items in the same format as those of the table in FIG. 7. In addition, the reference numerals such as L01 or L02 in FIG. 12 represent the same components as those in FIG. 7. FIG. 13 is a table representing various numerical data of the objective optical system in FIG. 11. FIG. 13 illustrates various numerical data of the objective optical system when the curvature radii of the meniscus lens are represented by R1 and R2 and the thickness thereof is represented by d. FIG. 13 is a table in the same format as that of FIG. 8.

As illustrated in FIG. 12, the first group optical system includes a lens having an Abbe number v1 of 35 or higher (having a low dispersion), and the second group optical system includes a lens having an Abbe number v2 of 45 or lower (having a high dispersion).

The first lens L11 of a distal end of the first group optical system toward the object side is a meniscus lens, and a ratio of the curvature radius R1 of the meniscus lens on the distal end side to the curvature radius R2 of the meniscus lens on the proximal end side is 3.69, which is higher than or equal to 3.

Figure 14:
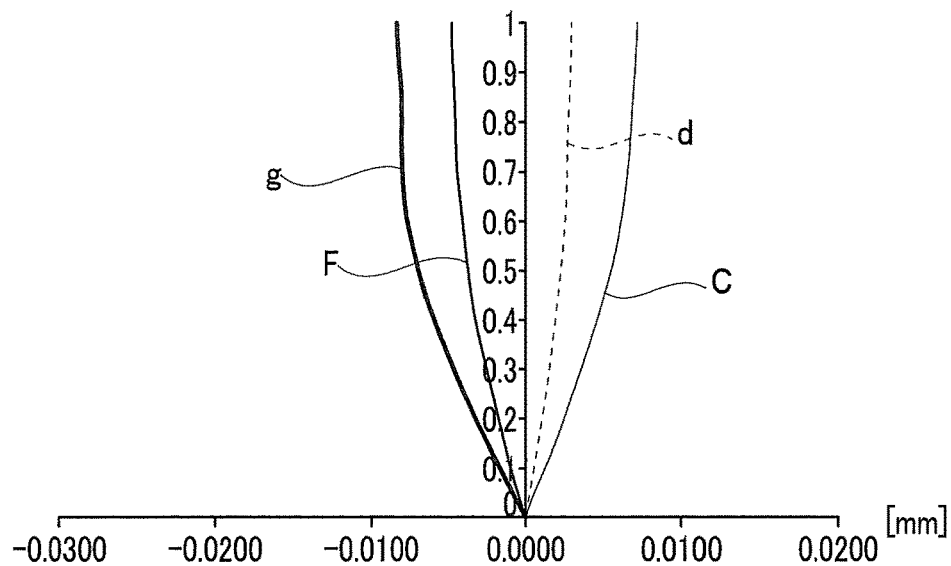
FIG. 14 is a graph illustrating a lateral chromatic aberration of the objective optical system in the second embodiment of the present invention.

FIG. 14 is a graph illustrating lateral chromatic aberration of the objective optical system in FIG. 11. FIG. 14 is a graph illustrating the amount of shift (lateral chromatic aberration) on the image plane with respect to an e-ray (light having a wavelength of 0.546 μm). In FIG. 14, g represents the amount of shift of a g-ray having a wavelength of 0.436 μm, F represents the amount of shift of an F-ray having a wavelength of 0.486 μm, d represents the amount of shift of a d-ray having a wavelength of 0.588 μm, and C represents the amount of shift of a C-ray having a wavelength of 0.656 μm.

Figure 15:
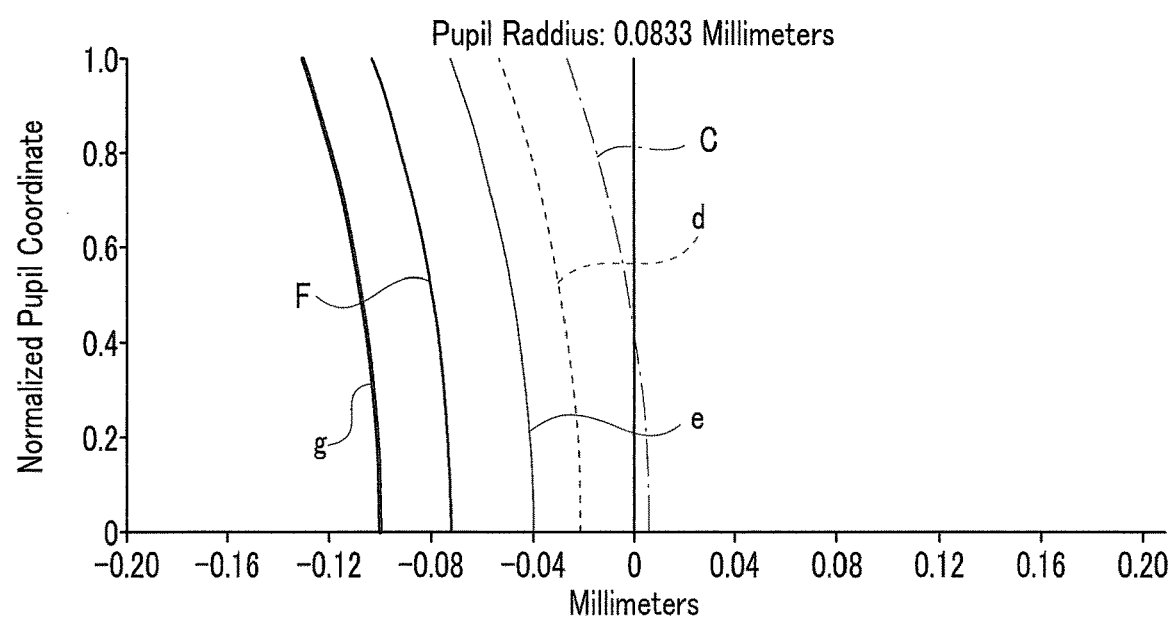
FIG. 15 is a graph illustrating an axial chromatic aberration of the objective optical system in the second embodiment of the present invention.

The amount of shift is 15 μm at most, and the chromatic aberration is slightly corrected at a level of a pixel size (several micrometers). FIG. 15 is a graph illustrating an axial chromatic aberration of the objective optical system in FIG. 11.

In addition, as illustrated in FIG. 13, a ratio of the curvature radius R1 of the spherical surface of the lens L11 on the distal end side to the curvature radius R2 of the spherical surface of the lens L11 as the meniscus lens on the proximal end side is 3 or higher. Here, (8.71/2.356)=3.69.

Further, as illustrated in FIG. 13, the curvature radius R1 of the spherical surface of the lens L11 on the distal end side is more than a value obtained by adding the thickness d of the lens L11 on the optical axis to the curvature radius R2 of the spherical surface of the lens L11 on the proximal end side. In other words, the sum of the curvature radius R2 of the Lens L11 on the proximal end side and the thickness d of the lens L11 along the optical axis is less than the curvature radius R1 of the lens L11 on the distal end side. In other words, |R1|>(|R2|+d). Here, 8.71>(2.36+0.90).

In addition, a ratio (max (L11, L12, L13)/min (L11, L12, L13)) of a maximum power to a minimum power in the three lenses L11, L12, and L13 of the concave lens group G1 is 3 or lower. Here, the ratio is 1.26.

Accordingly, with the objective optical system according to the present embodiment, the following operation and effects can be obtained.

1) Since the convex lens group G2 is on the image side of the concave lens group G1, the light flux diameter of a marginal light ray in the optical adaptor 31 can be reduced.

2) As the aperture AP in the optical adaptor 31 approaches the front of the objective optical system, the outer diameter of the distal end portion 11 can be reduced while maintaining the angle of view of the objective optical system.

3) The lens L14 as the convex lens that is spaced forward from the aperture AP has a high dispersion.

4) The lenses L12 and L13 as the concave lenses have low dispersion. The lens L11 as the meniscus lens is formed of a hard glass having a high refractive index and a medium dispersion.

As described above, the Abbe numbers of the lenses L11, L12, and L13 in the first group optical system are higher than or equal to 35 and specifically are 40.8, 67.7, and 67.7, respectively. The Abbe number of the lenses L14 in the second group optical system is lower than or equal to 45 and specifically is 40.8.

5) Even when the lens on the object side relative to the aperture AP has an ultra-wide angle, for example, an angle of view of 220 degrees, the light ray height is not high, and a power capable of achieving a reduction in diameter is obtained. The aperture AP is disposed in back of the lens L14, but a convex surface of the lens L14 is disposed to face the aperture side such that the light ray height decreases. In other words, the convex surface of the lens in front of the aperture faces the aperture AP. When seen from the image side, parallel light is adjusted to be thin as early as possible such that the light ray height decreases.

6) A convex lens close to the aperture AP does not act on a principal ray. Therefore, by partially reducing the diffusion of a principal ray using the convex surface of the lens L14 that is slightly spaced from the aperture AP and subsequently rapidly widening the angle using a convex air lens that is formed by the lenses L12 and L13 having concave surfaces facing each other, a reduction in the diameter of the optical adaptor 31 is realized.

Accordingly, with the present embodiment, in the optical adaptor 31, the number of concave lenses is 3, the number of convex lenses is 2, and the number of lenses can be reduced.

As described above, the present embodiment can provide an optical adaptor for endoscope that can suppress an increase in the number of lenses in the optical adaptor while favorably correcting chromatic aberration when mounted on the distal end portion of the insertion portion.

Third Embodiment

As in the second embodiment, the optical adaptor 31 according to a third embodiment includes five lenses, the number of which is less than the number of lenses in the first embodiment.

The configurations of the endoscope apparatus and the optical adaptor according to the present embodiment are the same as those of the endoscope apparatus and the optical adaptor according to the first embodiment except for the objective optical system. Therefore, the same components are represented by the same reference numerals, the description thereof will not be repeated, and only the configuration of the objective optical system will be described.

Figure 16:
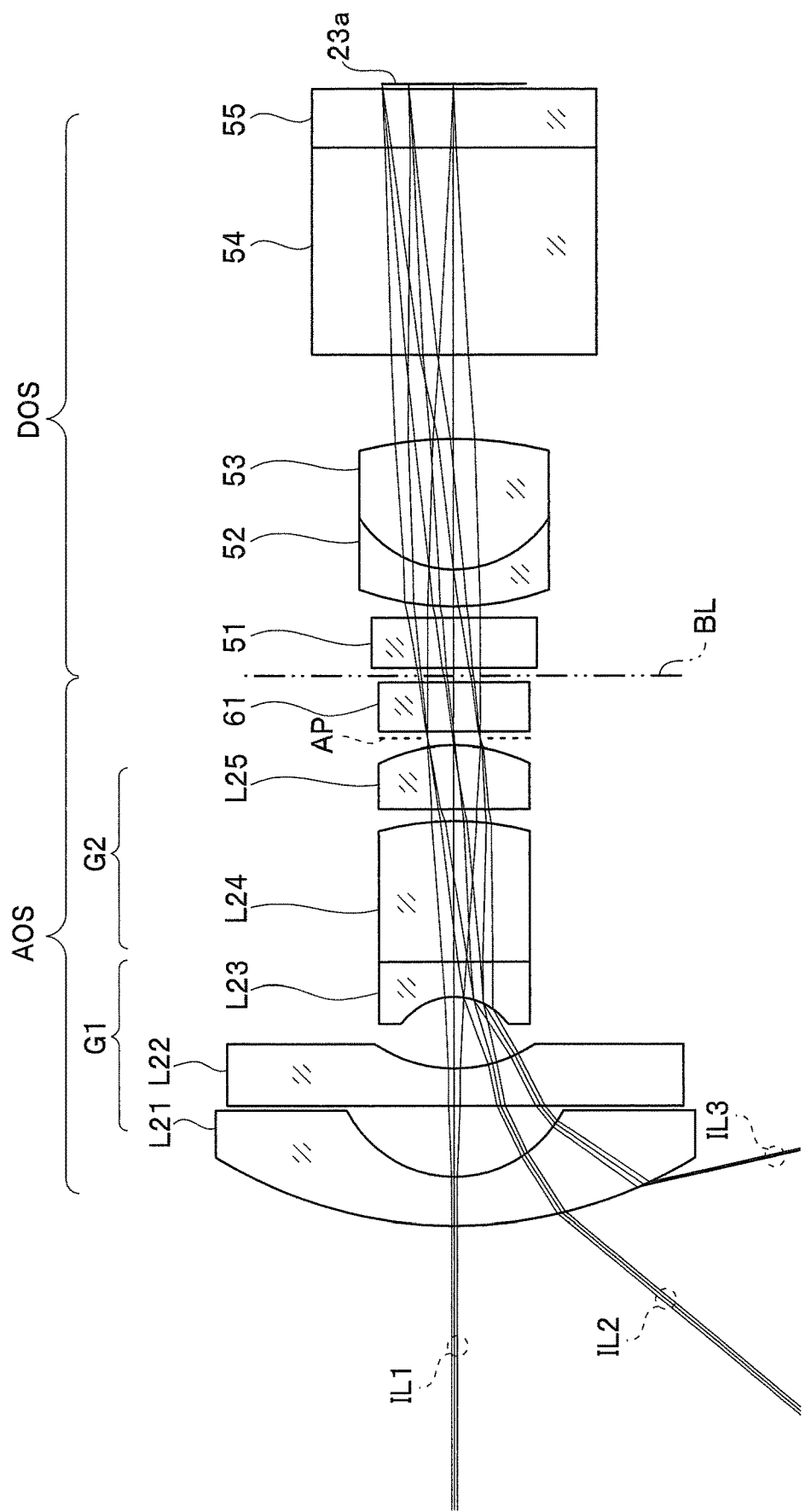
FIG. 16 is a diagram illustrating a configuration of an objective optical system in a third embodiment of the present invention.

FIG. 16 is a diagram illustrating the configuration of the objective optical system in the present embodiment. The optical system AOS of the optical adaptor 31 includes lenses L21 to L25 and the cover glass 61 in order from the distal end side. The lenses L21, L22, and L23 are a concave lens group G1, and the lenses L24 and L25 are a convex lens group G2. The angle of view of the concave lens group G1 is 220 degrees.

The lens L21 is a meniscus lens. The lens L22 is a plano-concave lens. The lens L23 is a concave flat lens. The lens L24 is a plano-convex lens. The lens L25 is a plano-convex lens. The aperture AP is disposed between the lens L25 and the cover glass 61. In other words, the first group optical system includes a meniscus lens (L21) disposed to be convex on the object side and a lens (L23) having a concave surface on the object side.

Light emitted from the optical adaptor 31 is parallel light and is incident on the optical system DOS of the distal end portion 11. In other words, the lenses L21 to L25 and the aperture AP configure an afocal optical system.

As described above, the optical adaptor 31 further includes the aperture AP and includes a first group optical system (concave lens group) having a negative combined focal length f as a whole and a second group optical system (convex lens group) having a positive combined focal length f as a whole in order from the object side.

FIG. 16 illustrates a light ray IL1 at 0 degrees, a light ray IL2 at 50 degrees, and a light ray IL3 at 100 degrees with respect to the optical axis of the objective optical system. Here, an F number of the objective optical system is 5.0. In the optical adaptor 31, the optical system AOS has a five-lens configuration, in which three concave lenses and two convex lenses are used. The number of lenses on the object side with respect to the aperture AP is 5, in which the number of concave lenses is 3 and the number of convex lenses is 2.

When a principal ray is traced from the image side of the objective optical system, the angle of the principal ray decreases toward the front of the aperture AP and subsequently rapidly increases. Therefore, by decreasing the height of the principal ray, a reduction in the diameter of the optical adaptor 31 can be realized.

The performance of the objective lens according to the present embodiment will be described. FIG. 17 is a table representing lens data of the objective optical system in FIG. 16. FIG. 17 is a table representing the same items in the same format as those of the table in FIG. 7. In addition, the reference numerals such as L01 or L02 in FIG. 17 represent the same components as those in FIG. 7. FIG. 18 is a table representing various numerical data of the objective optical system in FIG. 16. FIG. 18 illustrates various numerical data of the objective optical system when the curvature radii of the meniscus lens are represented by R1 and R2 and the thickness thereof is represented by d. FIG. 18 is a table in the same format as that of FIG. 8.

As illustrated in FIG. 17, the first group optical system (concave lens group G1) includes a lens having an Abbe number v1 of 35 or higher (having a low dispersion), and the second group optical system includes a lens having an Abbe number v2 of 45 or lower (having a high dispersion).

The first lens L21 of a distal end of the first group optical system toward the object side is a meniscus lens, and a ratio of the curvature radius R1 of the meniscus lens on the distal end side to the curvature radius R2 of the meniscus lens on the proximal end side is 3.69, which is higher than or equal to 3.

Figure 19:
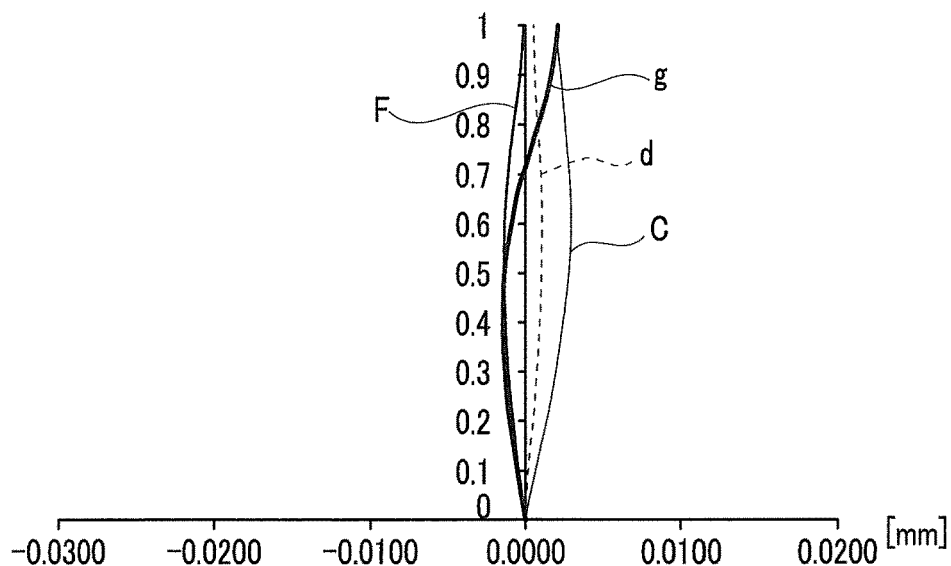
FIG. 19 is a graph illustrating lateral chromatic aberration of the objective optical system in the third embodiment of the present invention.

FIG. 19 is a graph illustrating lateral chromatic aberration of the objective optical system in FIG. 16. FIG. 19 illustrates the amount of shift (lateral chromatic aberration) on the image plane with respect to an e-ray (light having a wavelength of 0.546 μm). In FIG. 19, g represents the amount of shift of a g-ray having a wavelength of 0.436 μm, F represents the amount of shift of an F-ray having a wavelength of 0.486 μm, d represents the amount of shift of a d-ray having a wavelength of 0.588 μm, and C represents the amount of shift of a C-ray having a wavelength of 0.656 μm.

Figure 20:
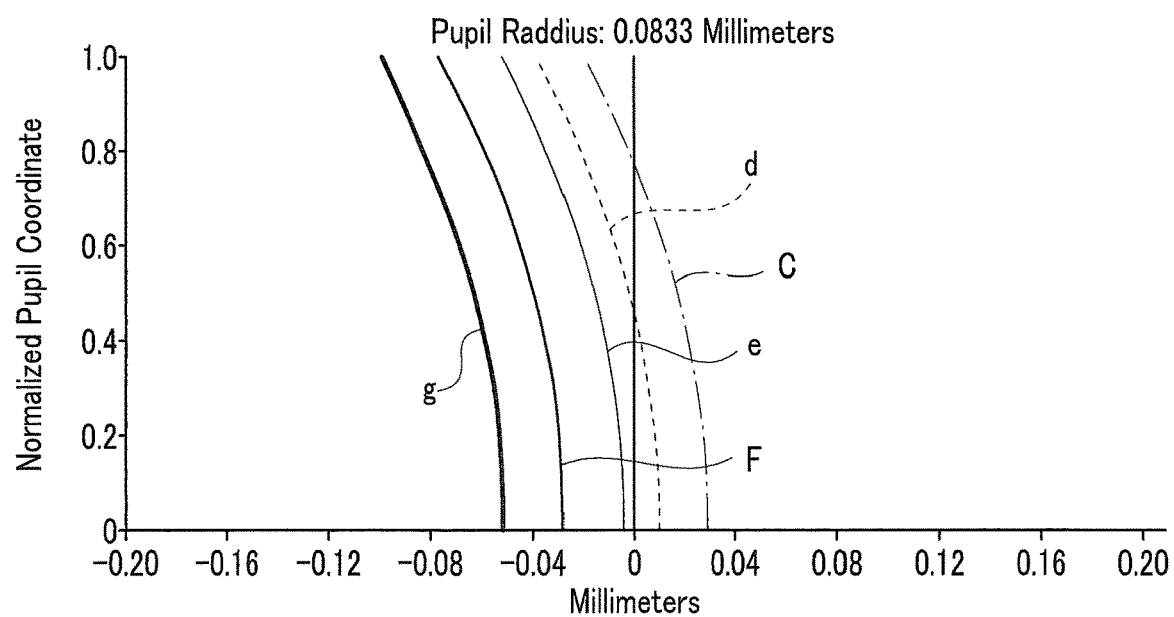
FIG. 20 is a graph illustrating an axial chromatic aberration of the objective optical system in the third embodiment of the present invention.

The amount of shift is 4 μm at most, and the chromatic aberration is favorably corrected at a level of a pixel size (several micrometers). FIG. 20 is a graph illustrating an axial chromatic aberration of the objective optical system in FIG. 16.

In addition, as illustrated in FIG. 18, a ratio of the curvature radius R1 of the spherical surface of the lens L21 on the distal end side to the curvature radius R2 of the spherical surface of the lens L21 as the meniscus lens on the proximal end side is 3 or higher. Here, (8.76/2.37)=3.69.

Further, as illustrated in FIG. 18, the curvature radius R1 of the spherical surface of the lens L21 on the distal end side is more than a value obtained by adding the thickness d of the lens L21 on the optical axis to the curvature radius R2 of the spherical surface of the lens L21 on the proximal end side. In other words, the sum of the curvature radius R2 of the Lens L21 on the proximal end side and the thickness d of the lens L21 along the optical axis is less than the curvature radius R1 of the lens L21 on the distal end side. In other words, |R1|>(|R2|+d). Here, 8.76>(2.37+0.91).

In addition, a ratio (max (L21, L22, L23)/min (L21, L22, L23)) of a maximum power to a minimum power in the three lenses L21, L22, and L23 of the concave lens group G1 is 3 or lower. Here, the ratio is 1.51.

As described above, the Abbe numbers of the lenses L21, L22, and L23 in the first group optical system are higher than or equal to 35 and specifically are 40.8, 55.5, and 55.5, respectively. The Abbe number of the lenses L24 in the second group optical system is lower than or equal to 45 and specifically is 18.9.

In particular, the Abbe numbers of the respective lenses L21, L22, and L23 as the lenses on the object side relative to the aperture AP are higher than the Abbe numbers of the respective lenses L24 and L25 as the lenses on the object side relative to the aperture AP by 20 or higher. Here, the difference in Abbe number is 31.7.

Accordingly, with the objective optical system according to the present embodiment, the following operation and effects can be obtained.

1) Since the convex lens group G2 is on the image side of the concave lens group G1, the light flux diameter of a marginal light ray in the optical adaptor 31 can be reduced.

2) By increasing the refractive indices of the lenses L22 and L23, the generation of spherical aberration is suppressed. On the other hand, the dispersion increases, and the correction of lateral chromatic aberration is insufficient. Therefore, the lenses L24 and L25 as the convex lenses in front of the aperture AP are provided. In order to correct the lateral chromatic aberration, the lenses L24 and L25 are formed of a material having a high dispersion. Further, since axial chromatic aberration is generated, the performance of the objective optical system as a whole is secured using the material.

Accordingly, with the present embodiment, in the optical adaptor 31, the number of concave lenses is 3, the number of convex lenses is 2, and the number of lenses can be reduced.

As described above, the present embodiment can provide an optical adaptor for endoscope that can suppress an increase in the number of lenses in the optical adaptor while favorably correcting chromatic aberration when mounted on the distal end portion of the insertion portion.

Fourth Embodiment

As in the second embodiment, the optical adaptor 31 according to a fourth embodiment includes five lenses, the number of which is less than the number of lenses in the first embodiment.

The configurations of the endoscope apparatus and the optical adaptor according to the present embodiment are the same as those of the endoscope apparatus and the optical adaptor according to the first embodiment except for the objective optical system. Therefore, the same components are represented by the same reference numerals, the description thereof will not be repeated, and only the configuration of the objective optical system will be described.

Figure 21:
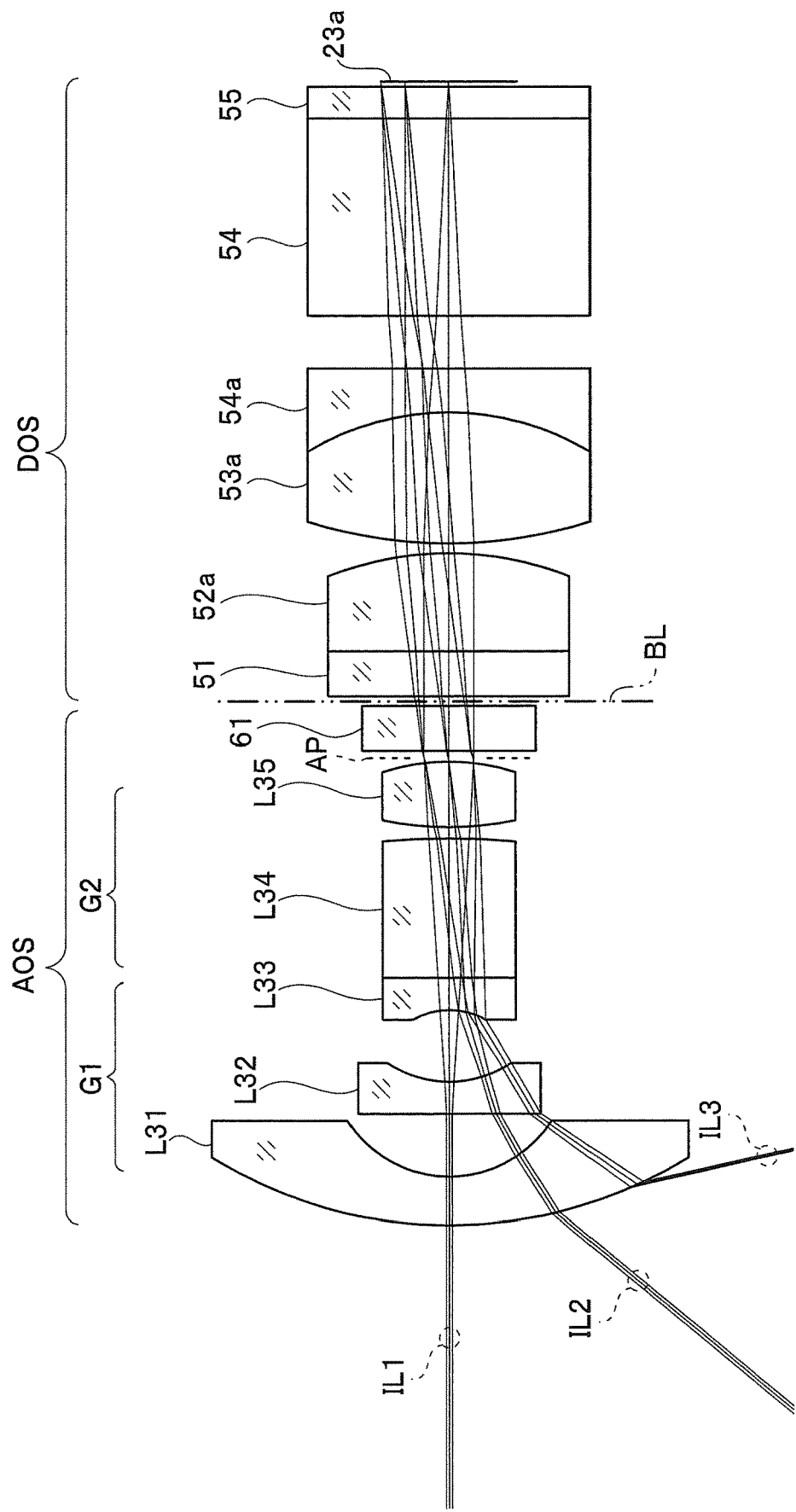
FIG. 21 is a diagram illustrating a configuration of an objective optical system in a fourth embodiment of the present invention.

FIG. 21 is a diagram illustrating the configuration of the objective optical system in the present embodiment. The optical system AOS of the optical adaptor 31 includes lenses L31 to L35 and the cover glass 61 in order from the distal end side. The lenses L31, L32, and L33 are a concave lens group G1, and the lenses L34 and L35 are a convex lens group G2. The angle of view of the concave lens group G1 is 220 degrees.

The lens L31 is a meniscus lens. The lens L32 is a plano-concave lens. The lens L33 is a concave flat lens. The lens L34 is a plano-convex lens. The lens L35 is a biconvex lens. The aperture AP is disposed between the lens L35 and the cover glass 61. In other words, the first group optical system includes a meniscus lens (L31) disposed to be convex on the object side and a lens (L33) having a concave surface on the object side.

In other words, the first group optical system includes a meniscus lens (L1) disposed to be convex on the object side and a lens (L3) having a concave surface on the object side.

Light emitted from the optical adaptor 31 is parallel light and is incident on the optical system DOS of the distal end portion. In other words, the lenses L31 to L35 and the aperture AP configure an afocal optical system.

As described above, the optical adaptor 31 further includes the aperture AP and includes a first group optical system (concave lens group) having a negative combined focal length f as a whole and a second group optical system (convex lens group) having a positive combined focal length f as a whole in order from the object side.

FIG. 21 illustrates a light ray IL1 at 0 degrees, a light ray IL2 at 50 degrees, and a light ray IL3 at 100 degrees with respect to the optical axis of the objective optical system. Here, an F number of the objective optical system is 5.0. In the optical adaptor 31, the optical system AOS has a five-lens configuration, in which three concave lenses and two convex lenses are used. The number of lenses on the object side with respect to the aperture AP is 5, in which the number of concave lenses is 3 and the number of convex lenses is 2.

When a principal ray is traced from the image side of the objective optical system, the angle of the principal ray decreases toward the object side relative to the aperture AP and subsequently rapidly increases. Therefore, by decreasing the height of the principal ray, a reduction in the diameter of the optical adaptor 31 can be realized.

In the present embodiment, the configuration of the optical system DOS in the distal end portion 11 is different from that of the optical system DOS in FIG. 16. In the optical system DOS, the cover glass 51, a plano-convex lens 52a, a biconvex lens 53a, a concave flat lens 54a, the protective glass 54, and the cover glass 55 are disposed in order from the distal end side.

The performance of the objective lens according to the present embodiment will be described. FIG. 22 is a table representing lens data of the objective optical system in FIG. 21. FIG. 22 is a table representing the same items in the same format as those of the table in FIG. 7. In addition, the reference numerals such as L01 or L02 in FIG. 22 represent the same components as those in FIG. 7. FIG. 23 is a table representing various numerical data of the objective optical system in FIG. 21. FIG. 23 illustrates various numerical data of the objective optical system when the curvature radii of the meniscus lens are represented by R1 and R2 and the thickness thereof is represented by d. FIG. 23 is a table in the same format as that of FIG. 8.

As illustrated in FIG. 22, the first group optical system (concave lens group G1) includes a lens having an Abbe number ν1 of 35 or higher (having a low dispersion), and the second group optical system includes a lens having an Abbe number ν2 of 45 or lower (having a high dispersion).

The first lens L31 of a distal end of the first group optical system toward the object side is a meniscus lens, and a ratio of the curvature radius R1 of the meniscus lens on the distal end side to the curvature radius R2 of the meniscus lens on the proximal end side is 3.37, which is higher than or equal to 3.

Figure 24:
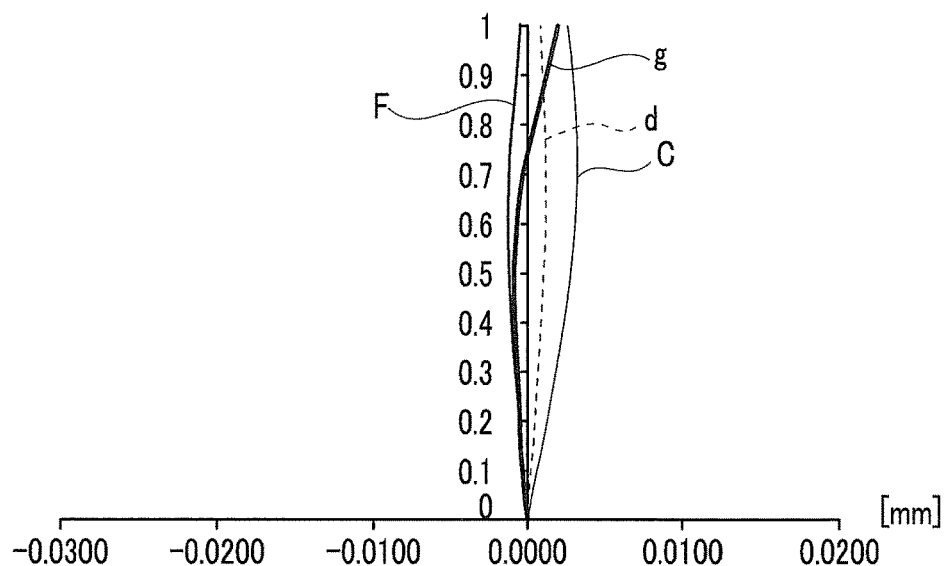
FIG. 24 is a graph illustrating lateral chromatic aberration of the objective optical system in the fourth embodiment of the present invention.

FIG. 24 is a graph illustrating a lateral chromatic aberration of the objective optical system in FIG. 21. FIG. 24 illustrates the amount of shift (lateral chromatic aberration) on the image plane with respect to an e-ray (light having a wavelength of 0.546 μm). In FIG. 24, g represents the amount of shift of a g-ray having a wavelength of 0.436 μm, F represents the amount of shift of an F-ray having a wavelength of 0.486 μm, d represents the amount of shift of a d-ray having a wavelength of 0.588 μm, and C represents the amount of shift of a C-ray having a wavelength of 0.656 μm.

Figure 25:
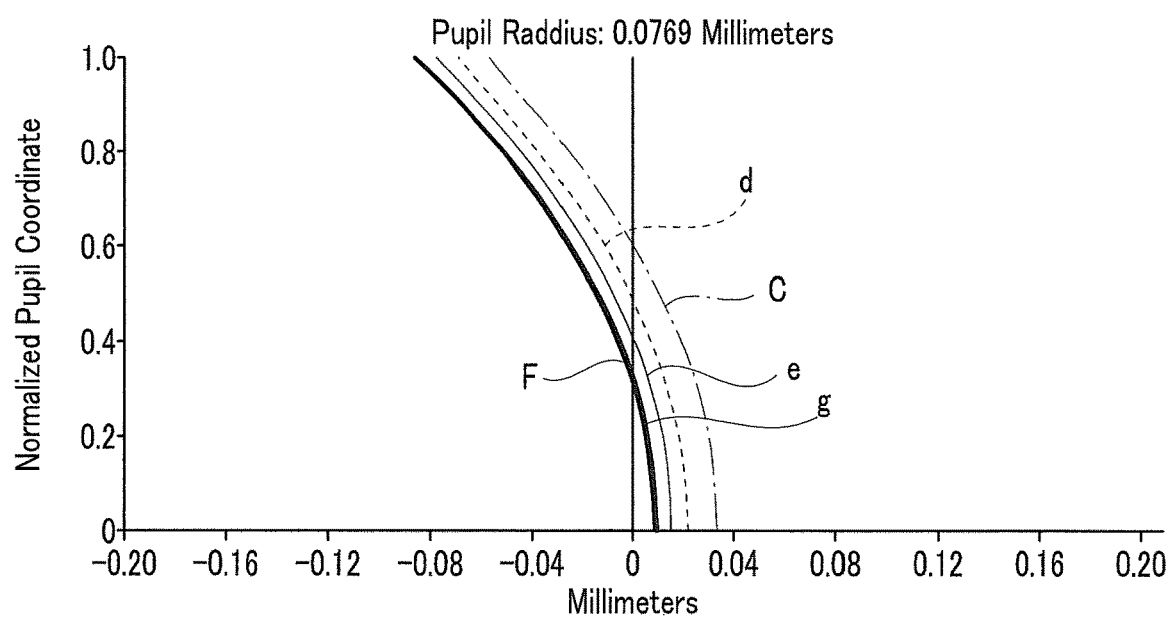
FIG. 25 is a graph illustrating an axial chromatic aberration of the objective optical system in the fourth embodiment of the present invention.

The amount of shift is 4 μm at most, and the chromatic aberration is favorably corrected at a level of a pixel size (several micrometers). FIG. 25 is a graph illustrating an axial chromatic aberration of the objective optical system in FIG. 21.

In addition, as illustrated in FIG. 23, a ratio of the curvature radius R1 of the spherical surface of the meniscus lens on the distal end side to the curvature radius R2 of the spherical surface of the lens L31 as the meniscus lens on the proximal end side is 3 or higher. Here, (8.00/2.37)=3.38.

Further, as illustrated in FIG. 23, the curvature radius R1 of the spherical surface of the lens L31 on the distal end side is more than a value obtained by adding the thickness d of the lens L31 on the optical axis to the curvature radius R2 of the spherical surface of the lens L31 on the proximal end side. In other words, the sum of the curvature radius R2 of the Lens L31 on the proximal end side and the thickness d of the lens L31 along the optical axis is less than the curvature radius R1 of the lens L31 on the distal end side. In other words, $|R1|>(|R2|+d)$. Here, 8.00>(2.37+0.83).

In addition, a ratio (max (L31, L32, L33)/min (L31, L32, L33)) of a maximum power to a minimum power in the three lenses L31, L32, and L33 of the concave lens group G1 is 3 or lower. Here, the ratio is 1.45.

Accordingly, with the objective optical system according to the present embodiment, the same operation and effects as those of the third embodiment can be obtained.

In particular, in the present embodiment, the Abbe numbers of the lenses L31, L32, and L33 in the first group optical system are higher than or equal to 35 and specifically are 40.8, 50.6, and 55.5, respectively. The Abbe number of the lenses L34 in the second group optical system is lower than or equal to 45 and specifically is 18.9.

Accordingly, with the present embodiment, in the optical adaptor 31, the number of concave lenses is 3, the number of convex lenses is 2, and the number of lenses can be reduced.

As described above, the present embodiment can provide an optical adaptor for endoscope that can suppress an increase in the number of lenses in the optical adaptor while favorably correcting chromatic aberration when mounted on the distal end portion of the insertion portion.

Fifth Embodiment

The optical adaptor 31 according to the first embodiment includes six lenses. The optical adaptor 31 according to a fifth embodiment includes four lenses, the number of which is less than the number of lenses in the second, third, and fourth embodiments. Among two convex lenses, one convex lens is disposed in front of the aperture.

The configurations of the endoscope apparatus and the optical adaptor according to the present embodiment are the same as those of the endoscope apparatus and the optical adaptor according to the first embodiment except for the objective optical system. Therefore, the same components are represented by the same reference numerals, the description thereof will not be repeated, and only the configuration of the objective optical system will be described.

Figure 26:
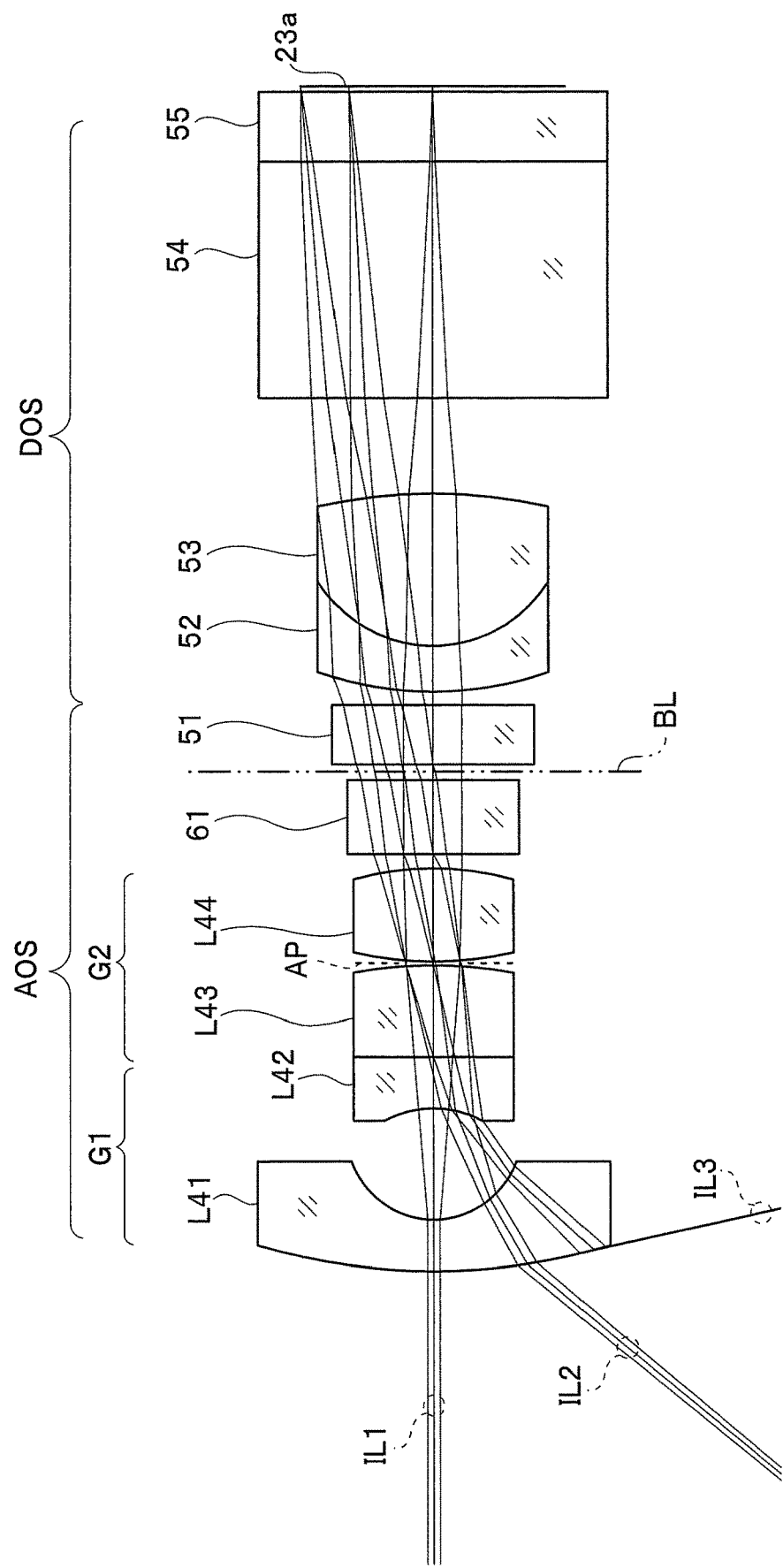
FIG. 26 is a diagram illustrating a configuration of an objective optical system in a fifth embodiment of the present invention.

FIG. 26 is a diagram illustrating the configuration of the objective optical system in the present embodiment. The optical system AOS of the optical adaptor 31 includes lenses L41 to L44 and the cover glass 61 in order from the distal end side. The lenses L41 and L42 are a concave lens group G1, and the lenses L43 and L44 are a convex lens group G2. The angle of view of the concave lens group G1 is 220 degrees.

The lens L41 is a meniscus lens. The lens L42 is a concave flat lens. The lens L43 is a plano-convex lens. The lens L44 is a biconvex lens. The aperture AP is disposed between the lenses L43 and L44. In other words, the first group optical system includes a meniscus lens (L41) disposed to be convex on the object side and a lens (L42) having a concave surface on the object side.

Light emitted from the optical adaptor 31 is parallel light and is incident on the optical system DOS of the distal end portion 11. In other words, the lenses L41 to L44 and the aperture AP configure an afocal optical system.

As described above, the optical adaptor 31 further includes the aperture AP and includes a first group optical system (concave lens group) having a negative combined focal length f as a whole and a second group optical system (convex lens group) having a positive combined focal length f as a whole in order from the object side.

FIG. 26 illustrates a light ray IL1 at 0 degrees, a light ray IL2 at 50 degrees, and a light ray IL3 at 100 degrees with respect to the optical axis of the objective optical system. Here, an F number of the objective optical system is 5.0. In the optical adaptor 31, the optical system AOS has a four-lens configuration, in which two concave lenses and two convex lenses are used. The number of lenses on the object side with respect to the aperture AP is 3, in which the number of concave lenses is 2 and the number of convex lenses is 1.

When a principal ray is traced from the image side of the objective optical system, the angle of the principal ray decreases toward the front of the aperture AP and subsequently rapidly increases. Therefore, by decreasing the height of the principal ray, a reduction in the diameter of the optical adaptor 31 can be realized.

The performance of the objective lens according to the present embodiment will be described. FIG. 27 is a table representing lens data of the objective optical system in FIG. 26. FIG. 27 is a table representing the same items in the same format as those of the table in FIG. 7. In addition, the reference numerals such as L01 or L02 in FIG. 27 represent the same components as those in FIG. 7. FIG. 28 is a table representing various numerical data of the objective optical system in FIG. 26. FIG. 28 illustrates various numerical data of the objective optical system when the curvature radii of the meniscus lens are represented by R1 and R2 and the thickness thereof is represented by d. FIG. 28 is a table in the same format as that of FIG. 8.

As illustrated in FIG. 27, the first group optical system (concave lens group G1) includes a lens having an Abbe number v1 of 35 or higher (having a low dispersion), and the second group optical system includes a lens having an Abbe number v2 of 45 or lower (having a high dispersion).

The first lens L41 of a distal end of the first group optical system toward the object side is a meniscus lens, and a ratio of the curvature radius R1 of the meniscus lens on the distal end side to the curvature radius R2 of the meniscus lens on the proximal end side is 6.67, which is higher than or equal to 3.

Figure 29:
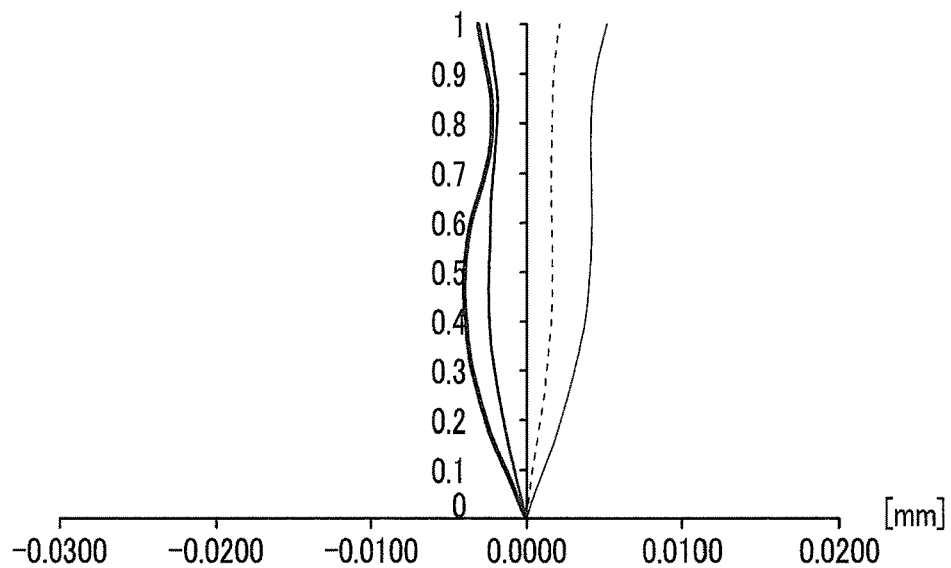
FIG. 29 is a graph illustrating lateral chromatic aberration of the objective optical system in the fifth embodiment of the present invention.

FIG. 29 is a graph illustrating lateral chromatic aberration of the objective optical system in FIG. 26. FIG. 29 illustrates the amount of shift (lateral chromatic aberration) on the image plane with respect to an e-ray (light having a wavelength of 0.546 µm). In FIG. 29, g represents the amount of shift of a g-ray having a wavelength of 0.436 µm, F represents the amount of shift of an F-ray having a wavelength of 0.486 µm, d represents the amount of shift of a d-ray having a wavelength of 0.588 µm, and C represents the amount of shift of a C-ray having a wavelength of 0.656 µm.

Figure 30:
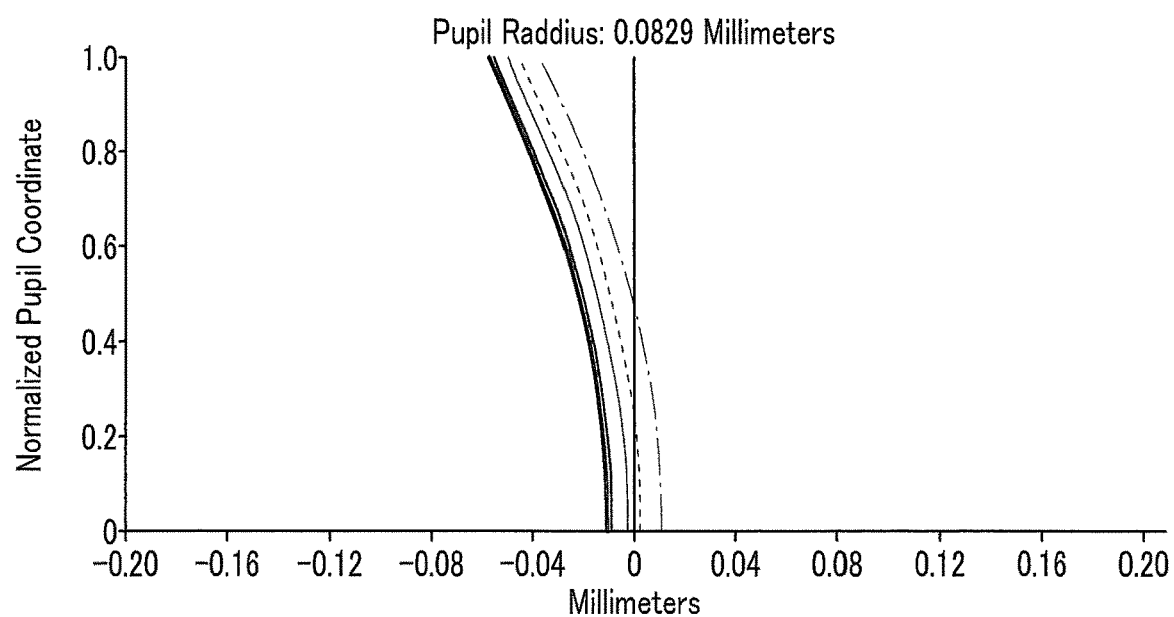
FIG. 30 is a graph illustrating an axial chromatic aberration of the objective optical system in the fifth embodiment of the present invention.

The amount of shift is 4 µm at most, and the chromatic aberration is favorably corrected at a level of a pixel size (several micrometers). FIG. 30 is a graph illustrating an axial chromatic aberration of the objective optical system in FIG. 26.

In addition, as illustrated in FIG. 28, a ratio of the curvature radius R1 of the spherical surface of the meniscus lens on the distal end side to the curvature radius R2 of the spherical surface of the lens L41 as the meniscus lens on the proximal end side is 3 or higher. Here, (5.56/0.83)=6.69.

Further, as illustrated in FIG. 28, the curvature radius R1 of the spherical surface of the lens L41 on the distal end side is more than a value obtained by adding the thickness d of the lens L41 on the optical axis to the curvature radius R2 of the spherical surface of the lens L41 on the proximal end side. In other words, the sum of the curvature radius R2 of the Lens L41 on the proximal end side and the thickness d of the lens L41 along the optical axis is less than the curvature radius R1 of the lens L41 on the distal end side. In other words, |R1|>(|R2|+d). Here, 5.56>(0.834+0.48).

In addition, a ratio (max (L41, L42)/min (L41, L42)) of a maximum power to a minimum power in the two lenses L41 and L42 of the concave lens group G1 is 3 or lower. Here, the ratio is 1.81.

As described above, the Abbe numbers of the lenses L41 and L42 in the first group optical system are higher than or equal to 35 and specifically are 40.8 and 64.1, respectively. The Abbe number of the lens L43 in the second group optical system is lower than or equal to 45 and specifically is 18.9.

In particular, the Abbe numbers of the respective lenses L41 and L42 as the lenses on the object side relative to the aperture AP are higher than the Abbe number of the lens L43 as the lens on the object side relative to the aperture AP by 20 or higher. Here, the difference in Abbe number is 26.8.

Accordingly, with the present embodiment, in the optical adaptor 31, the number of concave lenses is 2, the number of convex lenses is 2, and the number of lenses can be reduced.

As described above, the present embodiment can provide an optical adaptor for endoscope that can suppress an increase in the number of lenses in the optical adaptor while favorably correcting chromatic aberration when mounted on the distal end portion of the insertion portion.

Sixth Embodiment

The optical adaptor 31 according to the first embodiment includes six lenses. As in the fifth embodiment, the optical adaptor 31 according to a sixth embodiment includes four lenses, the number of which is less than the number of lenses in the second, third, and fourth embodiments. Among two convex lenses, one convex lens is disposed in front of the aperture AP.

The configurations of the endoscope apparatus and the optical adaptor according to the present embodiment are the same as those of the endoscope apparatus and the optical adaptor according to the first embodiment except for the objective optical system. Therefore, the same components are represented by the same reference numerals, the description thereof will not be repeated, and only the configuration of the objective optical system will be described.

Figure 31:
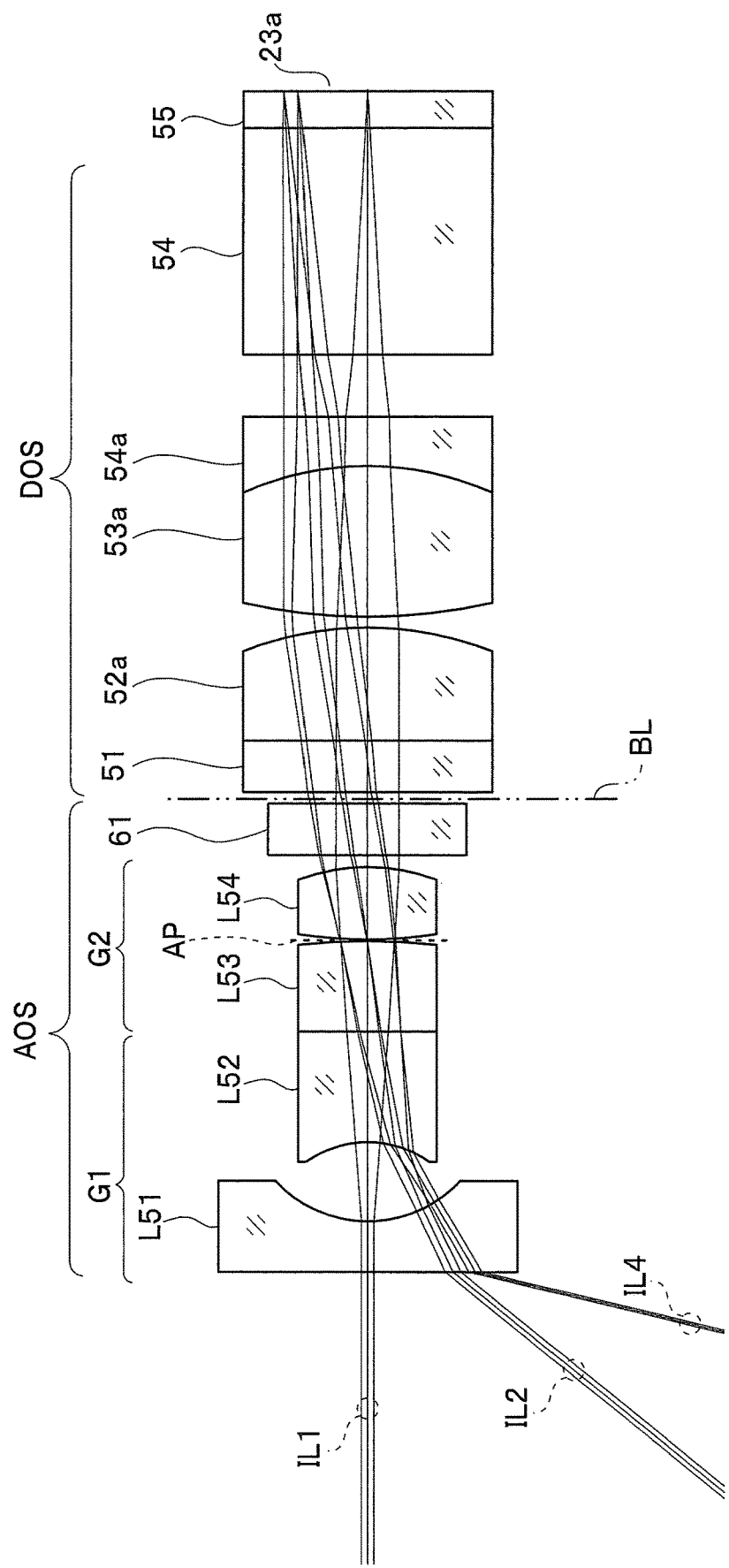
FIG. 31 is a diagram illustrating a configuration of an objective optical system in a sixth embodiment of the present invention.

FIG. 31 is a diagram illustrating the configuration of the objective optical system in the present embodiment. The optical system AOS of the optical adaptor 31 includes lenses L51 to L54 and the cover glass 61 in order from the distal end side. The lenses L51 and L52 are a concave lens group G1, and the lenses L53 and L54 are a convex lens group G2. The angle of view of the concave lens group G1 is 150 degrees.

The lens L51 is a plano-concave lens. The lens L52 is a concave flat lens. The lens L53 is a plano-convex lens. The lens L54 is a biconvex lens. The aperture AP is disposed between the lenses L53 and L54. The first group optical system includes a plano-concave lens (L51) having a plane on the object side and a lens (L52) having a concave surface on the object side. Light emitted from the optical adaptor 31 is parallel light and is incident on the optical system DOS of the distal end portion 11. In other words, the lenses L51 to L54 and the aperture AP configure an afocal optical system.

As described above, the optical adaptor 31 further includes the aperture AP and includes a first group optical system (concave lens group) having a negative combined focal length f as a whole and a second group optical system (convex lens group) having a positive combined focal length f as a whole in order from the object side.

FIG. 31 illustrates a light ray IL1 at 0 degrees, a light ray IL2 at 50 degrees, and a light ray IL4 at 75 degrees with respect to the optical axis of the objective optical system. Here, an F number of the objective optical system is 5.0. In the optical adaptor 31, the optical system AOS has a four-lens configuration, in which two concave lenses and two convex lenses are used. The number of lenses on the object side with respect to the aperture AP is 3, in which the number of concave lenses is 2 and the number of convex lenses is 1.

When a principal ray is traced from the image side of the objective optical system, the angle of the principal ray decreases toward the front of the aperture AP and subsequently rapidly increases. Therefore, by decreasing height of the principal ray, a reduction in the diameter of the optical adaptor 31 can be realized.

The performance of the objective lens according to the present embodiment will be described. FIG. 32 is a table representing lens data of the objective optical system in FIG. 31. FIG. 32 is a table representing the same items in the same format as those of the table in FIG. 7. In addition, the reference numerals such as L01 or L02 in FIG. 32 represent the same components as those in FIG. 7. FIG. 33 is a table representing various numerical data of the objective optical system in FIG. 31. FIG. 33 illustrates various numerical data of the objective optical system when the curvature radii of the lens L51 as the plano-concave lens are represented by R1 and R2 and the thickness thereof is represented by d. FIG. 33 is a table in the same format as that of FIG. 8.

As illustrated in FIG. 32, the first group optical system includes a lens having an Abbe number v1 of 35 or higher (having a low dispersion), and the second group optical system includes a lens having an Abbe number v2 of 45 or lower (having a high dispersion).

Figure 34:
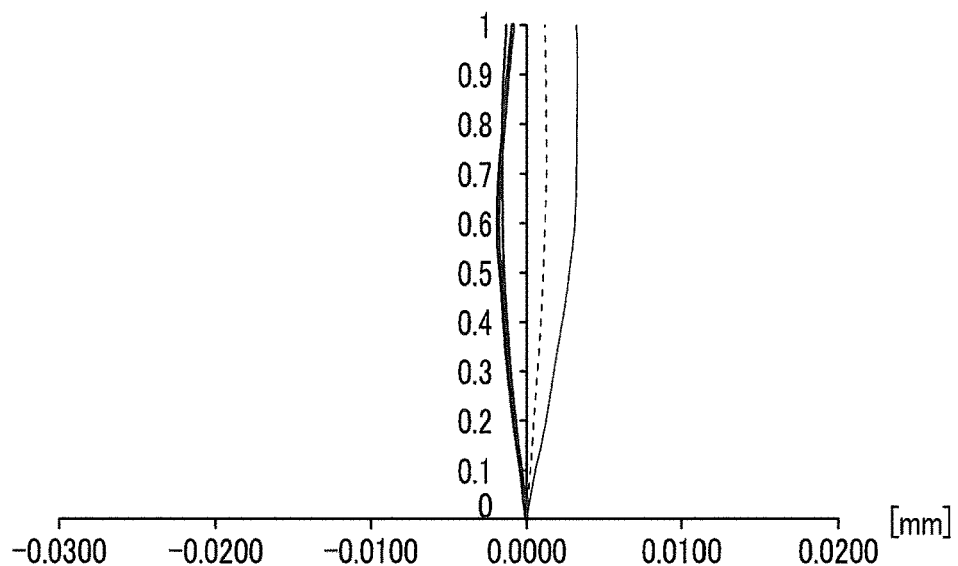
FIG. 34 is a graph illustrating lateral chromatic aberration of the objective optical system in the sixth embodiment of the present invention.

FIG. 34 is a graph illustrating lateral chromatic aberration of the objective optical system in FIG. 31. FIG. 34 illustrates the amount of shift (lateral chromatic aberration) on the image plane with respect to an e-ray (light having a wavelength of 0.546 µm). In FIG. 34, g represents the amount of shift of a g-ray having a wavelength of 0.436 µm, F represents the amount of shift of an F-ray having a wavelength of 0.486 µm, d represents the amount of shift of a d-ray having a wavelength of 0.588 µm, and C represents the amount of shift of a C-ray having a wavelength of 0.656 µm.

Figure 35:
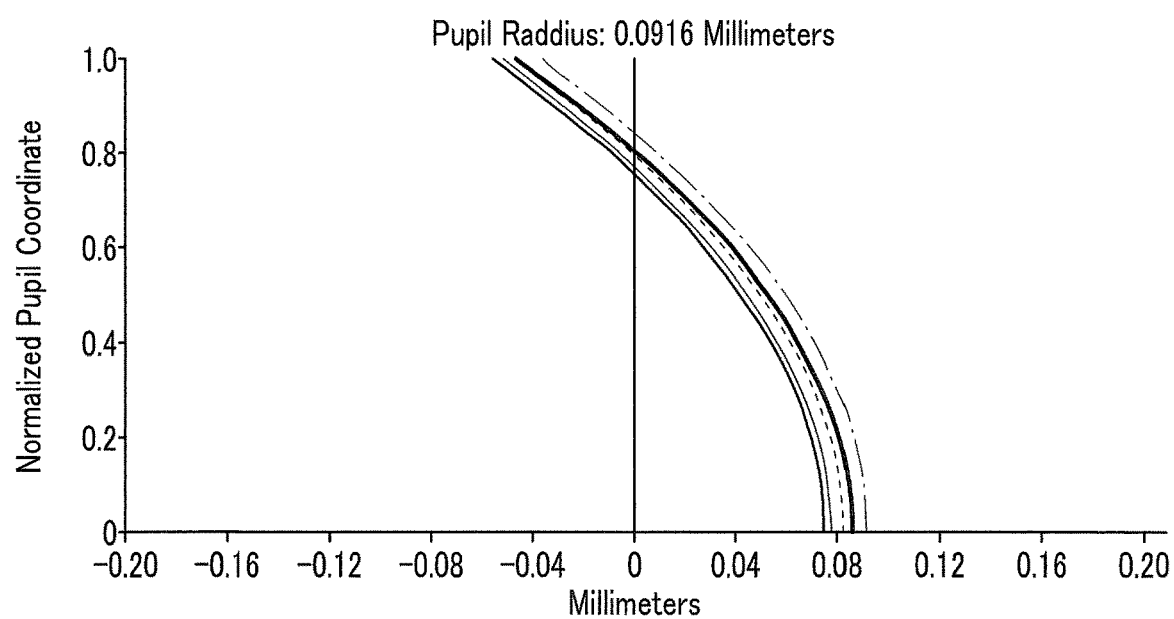
FIG. 35 is a graph illustrating an axial chromatic aberration of the objective optical system in the sixth embodiment of the present invention.

The amount of shift is 4 µm at most, and the chromatic aberration is favorably corrected at a level of a pixel size (several micrometers). FIG. 35 is a graph illustrating an axial chromatic aberration of the objective optical system in FIG. 31.

In addition, as illustrated in FIG. 33, a ratio of the curvature radius R1 of the spherical surface of the lens L51 on the distal end side to the curvature radius R2 of the spherical surface of the lens L51 as the meniscus lens on the proximal end side is 3 or higher. Here, ($\infty$/1.39)=$\infty$.

Further, as illustrated in FIG. 33, the curvature radius R1 of the spherical surface of the lens L51 on the distal end side is more than a value obtained by adding the thickness d of the lens L51 on the optical axis to the curvature radius R2 of the spherical surface of the lens L51 on the proximal end side. In other words, the sum of the curvature radius R2 of the Lens L51 on the proximal end side and the thickness d of the lens L51 along the optical axis is less than the curvature radius R1 of the lens L51 on the distal end side. In other words, $|R1|>(|R2|+d)$. Here, $\infty>(1.39+0.52)$.

In addition, a ratio (max (L51, L52)/min (L51, L52)) of a maximum power to a minimum power in the two lenses L51 and L52 of the concave lens group G1 is 3 or lower. Here, the ratio is 1.04.

As described above, the Abbe numbers of the lenses L51 and L52 in the first group optical system are higher than or equal to 35 and specifically are 40.8 and 64.1, respectively. The Abbe number of the lens L53 in the second group optical system is lower than or equal to 45 and specifically is 25.7.

In particular, the Abbe numbers of the respective lenses L51 and L52 as the lenses on the object side relative to the aperture AP are higher than the Abbe number of the lens L53 as the lens on the object side relative to the aperture AP by 20 or higher. Here, the difference in Abbe number is 33.6.

Accordingly, with the present embodiment, in the optical adaptor 31, the number of concave lenses is 2, the number of convex lenses is 2, and the number of lenses can be reduced.

As described above, the present embodiment can provide an optical adaptor for endoscope that can suppress an increase in the number of lenses in the optical adaptor while favorably correcting chromatic aberration when mounted on the distal end portion of the insertion portion.

As described above, the above-described embodiments can provide an optical adaptor for endoscope that can suppress an increase in the number of lenses in the optical adaptor while favorably correcting chromatic aberration when mounted on the distal end portion of the insertion portion.

Each of the lenses in the optical system for endoscope is small. Therefore, when the number of lenses increases, it is necessary to increase the processing accuracy of the lenses during the manufacturing of the optical system. According to the respective embodiments, the number of lenses can be reduced while favorably correcting chromatic aberration. Therefore, the need for high processing accuracy of the lenses can be reduced.

Figure 36:
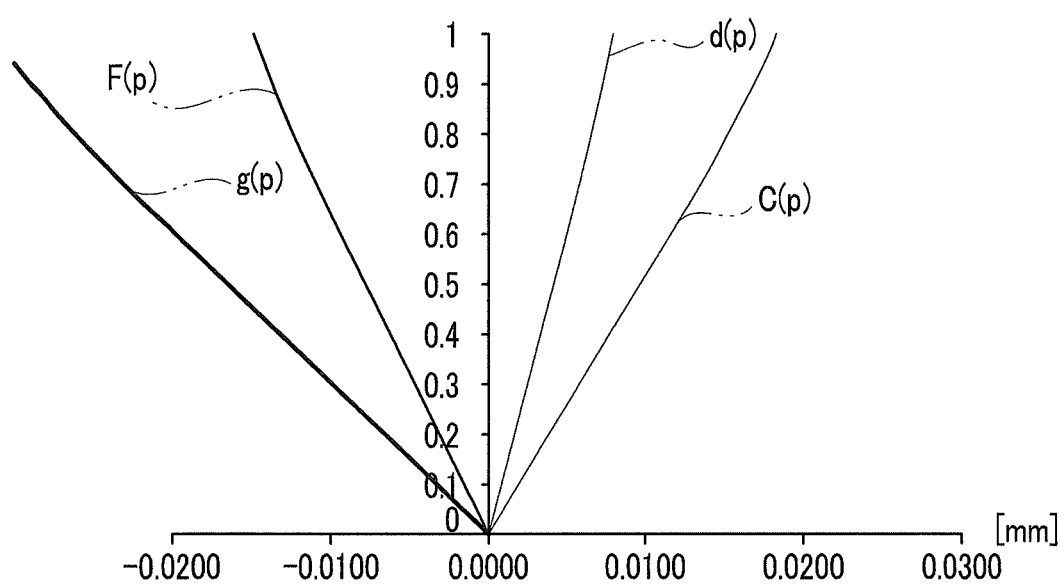
FIG. 36 is a graph illustrating an example of an axial chromatic aberration of an objective optical system including an optical adaptor in the related art.

FIG. 36 is a graph illustrating an example of an axial chromatic aberration of an objective optical system including an optical adaptor in the related art. As compared to an endoscope in which the angle of view of the objective optical system is widened using the optical adaptor in the related art, for example, an optical adaptor including two concave lenses and one convex lens and having an angle of view of 220 degrees and an F number of 5.5, when the Abbe numbers of the two concave lenses are 40.8 and 55.5 and the Abbe number of the one convex lens is 58.6, chromatic aberration is not corrected, and the sharpness of an endoscopic image is low.

When this optical adaptor is used, in FIG. 36, the amounts of shift of a g-ray, an F-ray, a d-ray, and a C-ray are represented by g(p), F(p), d(p), and C(p), respectively. In order to correct this chromatic aberration, it is necessary to use a large number of lenses. As a result, the length of a rigid portion in the adaptor increases, and the outer diameter of the adaptor increases.

However, with the respective embodiments, in the optical adaptor 31, the number of concave lenses is 3 or 2, the number of convex lenses is 3 or 2, and the number of lenses can be reduced while favorably correcting chromatic aberration.

The present invention is not limited to the above-described embodiments. For example, various changes and modifications can be made within a range not departing from the scope of the present invention.

What is claimed is:

1. An endoscope system comprising:
    a removable adaptor; and
    a main body optical system,
    wherein the adaptor includes an aperture, the adaptor further includes a first group optical system having a negative combined focal length as a whole and a second group optical system having a positive combined focal length as a whole in order from an object side,
    the main body optical system includes an imaging lens configured to form an image of a light flux on an image pickup sensor, the light flux being transmitted through the adaptor from an object being imaged,
    the first group optical system includes a lens having an Abbe number of 35 or higher, and
    the second group optical system includes a lens having an Abbe number of 45 or lower,
    the first group optical system includes, sequentially from the object side, a meniscus lens and two lenses having concave surfaces facing each other, and
    in the adaptor, the first group optical system, the second group optical system, and the aperture are disposed sequentially from the object side.

2. The endoscope system according to claim 1, wherein the meniscus lens is disposed to be convex on the object side.

3. The endoscope system according to claim 2, wherein a lens of a distal end of the first group optical system toward the object side is the meniscus lens, and a ratio of a curvature radius of the meniscus lens on the distal end side to a curvature radius of the meniscus lens on a proximal end side is 3 or higher.

4. The endoscope system according to claim 2, wherein in the first group optical system, the meniscus lens disposed to be convex on the object side and a lens having a concave surface on the object side are provided in order from the object side.

5. The endoscope system according to claim 1, wherein a ratio of a maximum power to a minimum power in a plurality of lenses included in the first group optical system is 3 or lower.

6. The endoscope system according to claim 1, wherein a lens of a distal end of the first group optical system toward the object side is the meniscus lens and a sum of a curvature radius of the meniscus lens on a proximal end side and a thickness of the meniscus lens along an optical axis is less than a curvature radius of the meniscus lens on a distal end side.

7. The endoscope system according to claim 1, wherein a difference between an Abbe number of the first group optical system and an Abbe number of the second group optical system is 20 or higher.

8. The endoscope system according to claim 1, wherein the first group optical system, the second group optical system, and the aperture configure an afocal optical system.

9. The endoscope system according to claim 1, wherein a number of lenses in the first group optical system is more than a number of lenses in the second group optical system by one.

10. The endoscope system according to claim 1, wherein an Abbe number of a lens in back of the aperture is higher than an Abbe number of the second group optical system.

11. The endoscope system according to claim 1, wherein an angle of view of the first group optical system on the object side is in a range of 200 degrees to 220 degrees.

12. The endoscope system according to claim 1, wherein an angle of view of the first group optical system on the object side is in a range of 140 degrees to 150 degrees.

13. The endoscope system according to claim 1, wherein each of the lenses of the first group optical system has an Abbe number of 35 or higher.

14. An optical adaptor for endoscope that is removable from a distal end portion of an insertion portion of an endoscope, the optical adaptor comprising:
    an aperture;
    a first group optical system having a negative combined focal length as a whole; and
    a second group optical system having a positive combined focal length as a whole, wherein
    the first group optical system and the second group optical system are provided in order from an object side,
    the first group optical system includes a lens having an Abbe number of 35 or higher, and
    the second group optical system includes a lens having an Abbe number of 45 or lower,
    wherein the first group optical system includes, sequentially from the object side, a meniscus lens and two lenses having concave surfaces facing each other, and
    in the adaptor, the first group optical system, the second group optical system, and the aperture are disposed sequentially from the object side.

15. The optical adaptor for endoscope according to claim 14, wherein each of the lenses of the first group optical system has an Abbe number of 35 or higher.

* * * * *